US012616822B2

(12) United States Patent
Lad et al.

(10) Patent No.: US 12,616,822 B2
(45) Date of Patent: May 5, 2026

(54) CEREBROSPINAL FLUID PURIFICATION SYSTEM

(71) Applicant: PHARAOH NUERO, INC., Minneapolis, MN (US)

(72) Inventors: Shivanand Lad, Durham, NC (US); William C. Mobley, La Jolla, CA (US); Karoly Nikolich, Emerald Hill, CA (US); Thomas Saul, El Granada, CA (US)

(73) Assignee: PHARAOH NEURO, INC., Minneapolis, MN (US)

( * ) Notice: Subject to any disclaimer, the term of this patent is extended or adjusted under 35 U.S.C. 154(b) by 883 days.

(21) Appl. No.: 17/354,429

(22) Filed: Jun. 22, 2021

(65) Prior Publication Data

US 2021/0386982 A1     Dec. 16, 2021

Related U.S. Application Data

(63) Continuation of application No. 16/548,554, filed on Aug. 22, 2019, now Pat. No. 11,065,425, which is a
(Continued)

(51) Int. Cl.
| | |
|---|---|
| *A61M 27/00* | (2006.01) |
| *A61M 25/00* | (2006.01) |
| *A61M 1/36* | (2006.01) |

(52) U.S. Cl.
CPC ...... *A61M 27/006* (2013.01); *A61M 25/0026* (2013.01); *A61M 1/3679* (2013.01);
(Continued)

(58) Field of Classification Search
CPC ............ A61M 27/006; A61M 25/0026; A61M 1/3679
See application file for complete search history.

(56) References Cited

U.S. PATENT DOCUMENTS

| | | | |
|---|---|---|---|
| 2,969,066 A | 1/1961 | Holter et al. | |
| 3,419,010 A | 12/1968 | Williamson | |
| | (Continued) | | |

FOREIGN PATENT DOCUMENTS

| | | | |
|---|---|---|---|
| CA | 2407214 A1 | 4/2003 | |
| CA | 2793672 A1 | 9/2011 | |
| | (Continued) | | |

OTHER PUBLICATIONS

Wollinsky, K. H., P. J. Hulser, et al. "CSF filtration is an effective treatment of Guillain-Barre syndrome: A randomized clinical trial," (2001). Neurology 57(5): 774-80. (Year: 2001).*
(Continued)

*Primary Examiner* — Ariana Zimbouski
(74) *Attorney, Agent, or Firm* — Seager, Tufte & Wickhem LLP

(57) ABSTRACT

The present invention provides methods and systems for conditioning cerebrospinal fluid (CSF) by removing target compounds from CSF. The systems provide for a catheter flow path and exchange of a majority volume portion of CSF in the CSF space. The removal and/or delivery of specific compounds can be tailored to the pathology of the specific disease. The removal is targeted and specific, for example, through the use of specific size-exclusion thresholds, antibodies against specific toxins, and other chromatographic techniques, as well as delivery and/or removal of targeted therapeutic agents.

20 Claims, 19 Drawing Sheets

Related U.S. Application Data continuation of application No. 15/410,219, filed on Jan. 19, 2017, now Pat. No. 10,398,884, which is a continuation of application No. 13/801,215, filed on Mar. 13, 2013, now Pat. No. 9,895,518, which is a continuation of application No. 12/444,581, filed as application No. PCT/US2007/080834 on Oct. 9, 2007, now Pat. No. 8,435,204.

(60) Provisional application No. 60/828,745, filed on Oct. 9, 2006.

(52) U.S. Cl.
CPC .............. *A61M 2025/0007* (2013.01); *A61M 2027/004* (2013.01); *A61M 2202/0021* (2013.01); *A61M 2202/0464* (2013.01); *A61M 2202/203* (2013.01); *A61M 2202/206* (2013.01); *A61M 2206/16* (2013.01); *A61M 2210/0693* (2013.01); *A61M 2210/1003* (2013.01)

(56)                    References Cited

U.S. PATENT DOCUMENTS

| | | | |
|---|---|---|---|
| 3,867,937 | A | 2/1975 | Schwartz |
| 3,889,687 | A | 6/1975 | Harris et al. |
| 4,378,797 | A | 4/1983 | Osterholm |
| 4,446,154 | A | 5/1984 | Osterholm |
| 4,451,251 | A | 5/1984 | Osterholm |
| 4,551,137 | A | 11/1985 | Osborne |
| 4,583,968 | A * | 4/1986 | Mahurkar .......... A61M 5/1582 |
| | | | 604/523 |
| 4,686,085 | A | 8/1987 | Osterholm |
| 4,767,409 | A | 8/1988 | Brooks |
| 4,830,849 | A | 5/1989 | Osterholm |
| 4,840,617 | A | 6/1989 | Osterholm |
| 4,888,115 | A | 12/1989 | Marinaccio et al. |
| 4,904,237 | A | 2/1990 | Janese |
| 4,950,232 | A | 8/1990 | Ruzicka et al. |
| 4,958,901 | A | 9/1990 | Coombs |
| 5,160,323 | A | 11/1992 | Andrew |
| 5,171,226 | A | 12/1992 | McCrory |
| 5,190,529 | A | 3/1993 | McCrory et al. |
| 5,334,315 | A * | 8/1994 | Matkovich .......... A61M 1/3647 |
| | | | 210/651 |
| 5,364,344 | A | 11/1994 | Beattie et al. |
| 5,396,899 | A | 3/1995 | Strittmatter |
| 5,405,316 | A | 4/1995 | Magram |
| 5,423,738 | A | 6/1995 | Robinson et al. |
| 5,462,667 | A | 10/1995 | Wollinsky et al. |
| 5,531,673 | A | 7/1996 | Helenowski |
| 5,584,314 | A | 12/1996 | Bron |
| 5,601,727 | A | 2/1997 | Bormann et al. |
| 5,683,357 | A | 11/1997 | Magram |
| 5,718,692 | A * | 2/1998 | Schon ................. A61M 25/007 |
| | | | 604/523 |
| 5,755,968 | A | 5/1998 | Stone |
| 5,772,607 | A | 6/1998 | Magram |
| 5,836,928 | A | 11/1998 | Gerber et al. |
| 5,897,528 | A | 4/1999 | Schultz |
| 5,941,853 | A | 8/1999 | Collins |
| 5,947,689 | A | 9/1999 | Schick |
| 5,948,441 | A | 9/1999 | Lenk et al. |
| 5,980,480 | A * | 11/1999 | Rubenstein ......... A61M 27/006 |
| | | | 604/9 |
| 6,013,051 | A | 1/2000 | Nelson |
| 6,056,725 | A | 5/2000 | Elsberry |
| 6,217,552 | B1 | 4/2001 | Barbut et al. |
| 6,238,382 | B1 | 5/2001 | Schock et al. |
| 6,264,625 | B1 | 7/2001 | Rubenstein et al. |
| 6,326,044 | B1 | 12/2001 | Lindquist |
| 6,379,331 | B2 | 4/2002 | Barbut et al. |
| 6,383,159 | B1 | 5/2002 | Saul et al. |
| 6,383,380 | B1 | 5/2002 | Kopf |
| 6,387,290 | B1 | 5/2002 | Brody et al. |
| 6,468,219 | B1 | 10/2002 | Njemanze |
| 6,517,529 | B1 | 2/2003 | Quinn |
| 6,537,241 | B1 | 3/2003 | Odland |
| 6,558,353 | B2 | 5/2003 | Zohmann |
| 6,575,928 | B2 | 6/2003 | Saul et al. |
| 6,594,880 | B2 | 7/2003 | Elsberry |
| 6,641,563 | B1 | 11/2003 | Vitullo et al. |
| 6,682,508 | B1 | 1/2004 | Meythaler et al. |
| 6,689,085 | B1 | 2/2004 | Rubenstein et al. |
| 6,689,756 | B2 | 2/2004 | Hesson et al. |
| 6,699,269 | B2 | 3/2004 | Khanna |
| 6,709,426 | B2 | 3/2004 | Gijsbers et al. |
| 6,758,832 | B2 | 7/2004 | Barbut et al. |
| 6,830,561 | B2 | 12/2004 | Jansen et al. |
| 6,849,185 | B1 | 2/2005 | Wu et al. |
| 6,875,192 | B1 | 4/2005 | Saul et al. |
| 6,969,383 | B2 | 11/2005 | Hildebrand |
| 7,011,647 | B2 | 3/2006 | Purdy et al. |
| 7,025,742 | B2 | 4/2006 | Rubenstein et al. |
| 7,108,680 | B2 | 9/2006 | Rohr et al. |
| 7,118,549 | B2 | 10/2006 | Chan |
| 7,150,737 | B2 | 12/2006 | Purdy et al. |
| 7,181,289 | B2 | 2/2007 | Pflueger et al. |
| 7,189,221 | B2 | 3/2007 | Silverberg et al. |
| 7,214,211 | B2 | 5/2007 | Woehr et al. |
| 7,252,659 | B2 | 8/2007 | Shehada et al. |
| 7,318,834 | B2 | 1/2008 | Njemanze |
| 7,455,666 | B2 | 11/2008 | Purdy |
| 7,708,716 | B2 | 5/2010 | Shah |
| 7,787,954 | B2 | 8/2010 | Purdy |
| 7,842,002 | B2 | 11/2010 | Mantle |
| 7,850,723 | B1 | 12/2010 | Magers |
| 7,887,503 | B2 | 2/2011 | Geiger |
| 8,029,495 | B2 | 10/2011 | Pyles |
| 8,131,353 | B2 | 3/2012 | Purdy |
| 8,137,334 | B2 | 3/2012 | Heruth et al. |
| 8,231,586 | B2 | 7/2012 | Kizer et al. |
| 8,357,296 | B2 | 1/2013 | Bonhomme et al. |
| 8,398,581 | B2 | 3/2013 | Panotopoulos |
| 8,435,204 | B2 | 5/2013 | Lad et al. |
| 8,444,661 | B2 | 5/2013 | Nair et al. |
| 8,475,419 | B2 | 7/2013 | Eckermann |
| 8,486,023 | B2 | 7/2013 | Pyles |
| 8,486,104 | B2 | 7/2013 | Samson et al. |
| 8,512,280 | B2 | 8/2013 | Rozenberg et al. |
| 8,518,636 | B2 | 8/2013 | Bosch et al. |
| 8,523,930 | B2 | 9/2013 | Saunders et al. |
| 8,603,057 | B2 | 12/2013 | Hoffman et al. |
| 8,669,044 | B2 | 3/2014 | Chiu et al. |
| 8,679,751 | B2 | 3/2014 | Haung |
| 8,721,642 | B1 | 5/2014 | Sullivan |
| 8,905,968 | B2 | 12/2014 | Thomas |
| 9,205,184 | B2 | 12/2015 | Eckermann |
| 9,211,163 | B1 | 12/2015 | Jaramaz et al. |
| 9,387,311 | B1 | 7/2016 | Heilman et al. |
| 2001/0020159 | A1 * | 9/2001 | Barbut ................ A61M 27/006 |
| | | | 604/113 |
| 2002/0123714 | A1 | 9/2002 | Saul et al. |
| 2002/0156482 | A1 | 10/2002 | Scribner et al. |
| 2002/0193285 | A1 | 12/2002 | Hesson et al. |
| 2003/0004495 | A1 | 1/2003 | Saul |
| 2003/0014016 | A1 * | 1/2003 | Purdy ................... A61B 10/02 |
| | | | 604/9 |
| 2003/0028137 | A1 | 2/2003 | Levin |
| 2003/0032915 | A1 * | 2/2003 | Saul ...................... A61B 5/031 |
| | | | 604/9 |
| 2003/0065309 | A1 | 4/2003 | Barnitz |
| 2003/0072761 | A1 | 4/2003 | LeBowitz |
| 2003/0083698 | A1 | 5/2003 | Whitehurst et al. |
| 2003/0097082 | A1 | 5/2003 | Purdy et al. |
| 2003/0129134 | A1 | 7/2003 | Chenard et al. |
| 2003/0130577 | A1 | 7/2003 | Purdy et al. |
| 2003/0135196 | A1 * | 7/2003 | Hesson ................. A61K 31/02 |
| | | | 604/500 |
| 2003/0163181 | A1 | 8/2003 | Frazer et al. |
| 2003/0199802 | A1 | 10/2003 | Barbut |
| 2004/0015133 | A1 | 1/2004 | Karim |

(56)             References Cited

U.S. PATENT DOCUMENTS

| | | |
|---|---|---|
| 2004/0030279 A1 | 2/2004 | Rubenstein et al. |
| 2004/0068221 A1 | 4/2004 | Silverberg et al. |
| 2004/0138125 A1 | 7/2004 | Wang |
| 2004/0138728 A1 | 7/2004 | Wong et al. |
| 2004/0142906 A1 | 7/2004 | Wang |
| 2004/0210231 A1 | 10/2004 | Boucher et al. |
| 2004/0215162 A1 | 10/2004 | Putz |
| 2004/0220545 A1 | 11/2004 | Heruth et al. |
| 2005/0004504 A1 | 1/2005 | Frye et al. |
| 2005/0060006 A1 | 3/2005 | Pflueger et al. |
| 2005/0090801 A1 | 4/2005 | Racz et al. |
| 2005/0095246 A1* | 5/2005 | Shafer ............... G01N 33/6863 |
| | | 604/890.1 |
| 2005/0256447 A1 | 11/2005 | Richardson et al. |
| 2006/0015160 A1 | 1/2006 | Lamard |
| 2006/0030027 A1* | 2/2006 | Ellson ................. A61M 1/3633 |
| | | 424/140.1 |
| 2006/0057142 A1 | 3/2006 | Brady et al. |
| 2006/0058836 A1 | 3/2006 | Bose et al. |
| 2006/0111659 A1* | 5/2006 | Tyler .................... A61B 5/6864 |
| | | 604/9 |
| 2006/0142783 A1 | 6/2006 | Lewis et al. |
| 2006/0161107 A1* | 7/2006 | Mantle ...................... A61F 7/12 |
| | | 604/113 |
| 2006/0175543 A1 | 8/2006 | Elefteriades |
| 2006/0184098 A1 | 8/2006 | Barnitz et al. |
| 2006/0224101 A1 | 10/2006 | Glenn |
| 2006/0282043 A1 | 12/2006 | Pyles |
| 2007/0050002 A1 | 3/2007 | Elefteriades |
| 2007/0246406 A1 | 10/2007 | Dibel et al. |
| 2008/0045883 A1 | 2/2008 | Radojicic |
| 2008/0154181 A1 | 6/2008 | Khanna |
| 2008/0171990 A1 | 7/2008 | Zauner |
| 2008/0249458 A1 | 10/2008 | Yamasaki |
| 2008/0249501 A1 | 10/2008 | Yamasaki |
| 2008/0319376 A1 | 12/2008 | Wilcox et al. |
| 2009/0076357 A1 | 3/2009 | Purdy |
| 2009/0082800 A1 | 3/2009 | Janardhan |
| 2009/0171369 A1 | 7/2009 | Gayzik |
| 2009/0277850 A1 | 11/2009 | Adams et al. |
| 2010/0030196 A1 | 2/2010 | Hildebrand et al. |
| 2010/0145267 A1 | 6/2010 | Bishop et al. |
| 2010/0168665 A1 | 7/2010 | Skerven |
| 2010/0179509 A1 | 7/2010 | Pyles |
| 2010/0198195 A1 | 8/2010 | Nishtala et al. |
| 2010/0204672 A1 | 8/2010 | Lockhart et al. |
| 2010/0260815 A1 | 10/2010 | Kyle et al. |
| 2010/0280438 A1 | 11/2010 | Thomas |
| 2010/0305492 A1 | 12/2010 | Lad et al. |
| 2010/0324397 A1 | 12/2010 | Purdy |
| 2011/0014635 A1 | 1/2011 | Suzuki et al. |
| 2011/0021991 A1* | 1/2011 | Sundstrom .......... A61M 27/006 |
| | | 604/151 |
| 2011/0029050 A1 | 2/2011 | Elefteriades et al. |
| 2011/0046547 A1 | 2/2011 | Mantle |
| 2011/0190831 A1 | 8/2011 | Mafi et al. |
| 2011/0319824 A1 | 12/2011 | Pyles |
| 2012/0004625 A1 | 1/2012 | Velez-Rivera |
| 2012/0149021 A1 | 6/2012 | Yung et al. |
| 2012/0165757 A1 | 6/2012 | Purdy |
| 2012/0203142 A1 | 8/2012 | Bedell |
| 2012/0203290 A1 | 8/2012 | Warren et al. |
| 2012/0209367 A1 | 8/2012 | Prindle et al. |
| 2012/0253266 A1 | 10/2012 | Qureshi et al. |
| 2012/0302938 A1 | 11/2012 | Browd et al. |
| 2012/0330196 A1 | 12/2012 | Nita |
| 2013/0023814 A1 | 1/2013 | Bertrand et al. |
| 2013/0030411 A1 | 1/2013 | Kreck et al. |
| 2013/0035628 A1 | 2/2013 | Garrison et al. |
| 2013/0066331 A1 | 3/2013 | Chitre et al. |
| 2013/0085413 A1 | 4/2013 | Tsamir et al. |
| 2013/0131811 A1 | 5/2013 | Barreiro et al. |
| 2013/0158470 A1 | 6/2013 | Panotopoulos |
| 2013/0158564 A1 | 6/2013 | Harries et al. |
| 2013/0165903 A1 | 6/2013 | Webler et al. |
| 2013/0197422 A1 | 8/2013 | Browd et al. |
| 2013/0248450 A1 | 9/2013 | Kenley et al. |
| 2014/0066830 A1 | 3/2014 | Lad et al. |
| 2014/0166555 A1 | 6/2014 | Dibel et al. |
| 2014/0194840 A1 | 7/2014 | Eckermann |
| 2014/0276334 A1 | 9/2014 | Eckermann |
| 2014/0276660 A1 | 9/2014 | Eckermann |
| 2014/0316373 A1 | 10/2014 | Dhall |
| 2014/0323857 A1 | 10/2014 | Mourad et al. |
| 2015/0196742 A1 | 7/2015 | Browd et al. |
| 2015/0223832 A1 | 8/2015 | Swaney et al. |
| 2015/0224284 A1 | 8/2015 | Panotopoulos et al. |
| 2015/0238685 A1 | 8/2015 | Elias et al. |
| 2015/0257774 A1 | 9/2015 | Galdonik et al. |
| 2016/0051801 A1 | 2/2016 | Vase |
| 2016/0101270 A1 | 4/2016 | Browd et al. |
| 2016/0136398 A1 | 5/2016 | Heilman et al. |
| 2016/0174995 A1 | 6/2016 | Turjman et al. |
| 2016/0303355 A1 | 10/2016 | Heilman et al. |
| 2016/0303356 A1 | 10/2016 | Heilman et al. |
| 2017/0000361 A1 | 1/2017 | Meyering et al. |
| 2017/0035950 A1 | 2/2017 | Meyering et al. |
| 2017/0035998 A1 | 2/2017 | Meyering et al. |
| 2017/0095649 A1 | 4/2017 | Vase et al. |
| 2017/0157374 A1 | 6/2017 | Hedstrom et al. |

FOREIGN PATENT DOCUMENTS

| | | | |
|---|---|---|---|
| CA | 2936349 A1 | 7/2015 | |
| CN | 101288783 A | 10/2008 | |
| CN | 101653637 A | 2/2010 | |
| CN | 202409608 U | 9/2012 | |
| CN | 102973305 A | 3/2013 | |
| CN | 203816046 U | 9/2014 | |
| CN | 203935243 U | 11/2014 | |
| CN | 105361923 A | 3/2016 | |
| EP | 515007 B1 | 12/1996 | |
| EP | 1180379 A1 * | 2/2002 | ........ A61M 25/0029 |
| EP | 1331019 A2 | 7/2003 | |
| EP | 2217315 B1 | 5/2012 | |
| EP | 2695633 A1 | 2/2014 | |
| EP | 2882483 B1 | 9/2016 | |
| GB | 2365344 A | 2/2002 | |
| JP | H03504681 A | 10/1991 | |
| JP | H08038595 A | 2/1996 | |
| JP | 2001509712 A | 7/2001 | |
| JP | 2001513349 A | 9/2001 | |
| JP | 2002514096 A | 5/2002 | |
| JP | 2003515394 A | 5/2003 | |
| JP | 2003250881 A | 9/2003 | |
| JP | 2003526398 A | 9/2003 | |
| JP | 2004508109 A | 3/2004 | |
| JP | 2004236792 A | 8/2004 | |
| JP | 2004528062 A | 9/2004 | |
| JP | 2006511292 A | 4/2006 | |
| JP | 2006525827 A | 11/2006 | |
| RU | 2100965 C1 | 1/1998 | |
| RU | 2158613 C2 | 11/2000 | |
| RU | 2290974 C1 | 1/2007 | |
| RU | 2312678 C1 | 12/2007 | |
| RU | 2314838 C2 | 1/2008 | |
| WO | 8909629 A1 | 10/1989 | |
| WO | 9205864 A1 | 4/1992 | |
| WO | 9802202 A1 | 1/1998 | |
| WO | 9833535 A1 | 8/1998 | |
| WO | 9907276 A2 | 2/1999 | |
| WO | 0041762 A1 | 7/2000 | |
| WO | 0043056 A1 | 7/2000 | |
| WO | 0051669 A1 | 9/2000 | |
| WO | 0139819 A2 | 6/2001 | |
| WO | 0154766 A1 | 8/2001 | |
| WO | 0211703 A1 | 2/2002 | |
| WO | 0220083 A2 | 3/2002 | |
| WO | 0232494 A2 | 4/2002 | |
| WO | 02056937 A2 | 7/2002 | |
| WO | 03015710 A2 | 2/2003 | |
| WO | 03020208 A2 | 3/2003 | |
| WO | 03057306 A1 | 7/2003 | |

(56) References Cited

FOREIGN PATENT DOCUMENTS

| WO | 2004043313 A3 | 5/2004 |
|----|---------------|--------|
| WO | 2004060463 A1 | 7/2004 |
| WO | 2004060465 A2 | 7/2004 |
| WO | 2004072647 A1 | 8/2004 |
| WO | 2004093945 A1 | 11/2004 |
| WO | 2004105839 A1 | 12/2004 |
| WO | 2005035025 A1 | 4/2005 |
| WO | 2005044335 A2 | 5/2005 |
| WO | 2005044847 A1 | 5/2005 |
| WO | 2006017763 A2 | 2/2006 |
| WO | 2006079007 A2 | 7/2006 |
| WO | 2006086195 A2 | 8/2006 |
| WO | 2007013945 A2 | 2/2007 |
| WO | 2007110643 A1 | 10/2007 |
| WO | 2008105959 A2 | 9/2008 |
| WO | 2009140202 A1 | 11/2009 |
| WO | 2009155614 A2 | 12/2009 |
| WO | 2010014447 A2 | 2/2010 |
| WO | 2010123558 A1 | 10/2010 |
| WO | 2010127071 A1 | 11/2010 |
| WO | 2010014447 A3 | 2/2011 |
| WO | 2011060317 A2 | 5/2011 |
| WO | 2011114260 A1 | 9/2011 |
| WO | 2011150323 A2 | 12/2011 |
| WO | 2012099984 A1 | 7/2012 |
| WO | 2013034602 A1 | 3/2013 |
| WO | 2013052951 A2 | 4/2013 |
| WO | 2014023551 A1 | 2/2014 |
| WO | 2014023552 A1 | 2/2014 |
| WO | 2014039780 A1 | 3/2014 |
| WO | 2014160481 A1 | 10/2014 |
| WO | 2015104631 A1 | 7/2015 |
| WO | 2015109260 A1 | 7/2015 |
| WO | 2015157320 A1 | 10/2015 |
| WO | 2016007553 A1 | 1/2016 |

OTHER PUBLICATIONS

Mascia, L., L. Fedoroko, et al. "Temporal Relationship Between Endothelin-1 Concentrations and Cerebral Vasospasm in Patients With Aneurysmal Subarachnoid Hemorrhage, Editorial Comment: Endothelin-1 in Vasospasm After SAH," (2001). Stroke 32(5):1185-90 (Year: 2001).*

M.A Firer, "Efficient elution of functional proteins in affinity chromatography," J. Biochem. Biophys. Methods, 49:433-442, 2001.

European Office Action for European Patent Application No. 07873762.4, 5 pages dated Dec. 7, 2016.

Mahon et al., "North American Clinical Experience with the EKOS MicroLysUS Infusion Catheter for the Treatment of Embolic Stroke," AJNR Am J. Neuroradiology, 24:534-538, Mar. 2003.

Rogers et al., "Percutaneous aspiration of brain tumor cysts via the Ommaya reservoir system, " Neurology, 41:279-282, Feb. 1991.

Japanese rejection of Appeal for related Japanese patent application No. 2009-531646, 13 pages, mailed Jan. 25, 2016.

International Search Report and Written Opinion dated Jun. 21, 2010 from International Patent Application No. PCT/US2010/001186.

Hansson et al., "Association between CSF biomarkers and incipient Alzheimer's disease in patients with mild cognitive impairment: a follow-up study," Lancert Neurol, 5:228-234, Mar. 2006.

European search report and opinion dated May 27, 2011, EP application No. 07873762.4.

International search report and written opinion dated Oct. 28, 2008 for International Patent Application No. PCT/US2007/080834.

Banci et al., "Metal-free superoxide dismutase forms soluble oligomers under physiological conditions: A possible general mechanism for familial ALS," Proc Natl Acad Sci US A, 104 (27): 11263-7, 2007.

Bayer et al., "Evaluation of the safety and immunogenicity of synthetic Aβ42 (AN1792) in patients with AD," Neurology, 64(1): 94-101, 2005.

Blennow et al., "Alzheimer's disease," Lancet, 368(9533): 387-403, 2006.

Caughey et al., "Protofibrils, pores, fibrils, and neurodegeneration: separating the responsible protein aggregates from the innocent bystanders," Annu Rev Neurosci, 26:267-98, 2003.

Dawson et al., "Molecular Pathways of Neurodegeneration in Parkinson's Disease," Science, 302 (5646):819-22, 2003.

Dekosky et al., "Looking Backward to Move Forward: Early Detection of Neurodegenerative Disorders," Science, 302 (5646):830-4, 2003.

Dias-Santagata et al., "Oxidative stress mediates tau-induced neurodegeneration in *Drosophila*," J. Clin Invest, 117(1):236-45, 2007.

Dunnet et al., "Prospects for new restorative and neuroprotective treatments in Parkinson's disease," Nature, 399(6738 Suppl):A32-9, 1999.

Gilman et al., "Clinical effects of Aβ immunization (AN1792) in patients with AD in an interrupted trial," Neurology, 64(9):1553-62, 2005.

Glabe, "Common mechanisms of amyloid oligomer pathogenesis in degenerative disease," Neurobiol Aging, 27(4):570-5, 2006.

Hock, "Antibodies against beta-amyloid slow cognitive decline in Alzheimer's disease," Neuron, 38(4):547-54, 2003.

Hohlfeld et al., "Autoimmune concepts of multiple sclerosis as a basis for selective immunotherapy: From pipe dreams to (therapeutic) pipelines," Proc Natl Acad Sci US A, 101(Suppl 2):14599-606, 2004.

Janus et al., "A beta peptide immunization reduces behavioural impairment and plaques in a model of Alzheimer's disease," Nature, 408(6815):979-82, 2000.

Kessler et al., "Endothelin-1 levels in plasma and cerebrospinal fluid of patients with cerebral vasospasm after aneurysmal subarachnoid hemorrhage," Surg Neural, 64(Suppl. 1)S1:2-5, 2005.

Koo et al., "Amyloid Diseases: Abnormal Protein Aggregation in Neurodegeneration," Proc Natl Acad Sci USA, 96(18):9989-90, 1999.

Kuwabara et al., "Intravenous Immunoglobulin Therapy for Guillain-Barre Syndrome with IgG anti-GM1 Antibody," Muscle Nerve, 24(1):54-8, 2001.

Macdonald et al., "Cerebral Vasospasm after Subarachnoid Hemorrhage: the Emerging Revolution," Nat Clin Pract Neural, 3(5):256-63, 2007.

Mascia et al., "Temporal Relationship Between Endothelin-1 Concentrations and Cerebral Vasospasm in Patients With Aneurysmal Subarachnoid Hemorrhage—Editorial Comment: Endothelin-1 in Vasospasm After SAH," Stroke, 32(5):1185-90, 2001.

Mcculloch et al., "A radical approach to stroke therapy," Proc Natl Acad Sci USA, 98(20):10989-91, 2001.

Mckhann et al., "Plasmapheresis and Guillain-Barre Syndrome: Analysis of Prognostic Factors and the Effect of Plasmapheresiss," Ann Neurol, 23(4):347-53, 1988.

Melnikova, "Therapies for Alzheimer's Disease," Nat Rev Drug Discov, 6(5):341-2, 2007.

Monsonego et al., "Immunotherapeutic Approches to Alzheimer's Disease," Science, 302(5646): 834-8, 2003.

Morgan et al., "A beta peptide vaccination prevents memory loss in an animal model of Alzheimer's disease," Nature, 408(6815):982-5, 2000.

Nicoll et al., "Abeta Species Removal after Abeta42 Immunization," J Neuropathol Exp Neurol, 65(11):1040-8, 2006.

Noseworthy, "Progress in Determining the Causes and Treatment of Multiple Sclerosis," Nature, 399(6738 Suppl): A40-7, 1999.

Orgogozo et al., "Subacute meningoencephalitis in a subset of patients with AD after Aβ42 immunization," Neurology, 61(1):46-54, 2003.

Parkhill et al., "The genome sequence of the food-borne pathogen Campylobacter jejuni reveals hypervariable sequences," Nature, 403(6770):665-8, 2000.

Roberson et al., "100 Years and Counting: Prospects for Defeating Alzheimer's Disease," Science, 314(5800):781-4, 2006.

Rowland, "Amyotrophic Lateral Sclerosis: Human Challenge for Neuroscience," Proc Natl Acad Sci USA, 92(5):1251-3, 1995.

(56)           References Cited

OTHER PUBLICATIONS

Shoulson, "Experimental Therapeutics of Neurodegenerative Disorders: Unmet Needs," Science, 282(5391):1072-4, 1998.

Steece-Collier et al., "Etiology of Parkinson's disease: Genetics and environment revisited," Proc Natl Acad Sci USA, 99(22):13972-4, 2002.

Taylor et al., "Toxic Proteins in Neurodegenerative Disease," Scient, 296(5575):1991-5, 2002.

Valentine et al., "Bioinorganic Chemistry Special Feature: Misfolded CuZnSOD and amyotrophic lateral sclerosis," Proc Natl Acad Sci USA, 100(7):3617-22, 2003.

Vernino et al., "Autoimmune Encephalopathies," Neurologist, 13(3):140-7, 2007.

Wollinsky et al., "CSF filtration is an effective treatment of Guillain-Barre syndrome: A randomized clinical trial," Neurology, 57(5):774-80, 2001.

Yuki et al., "Carbohydrate mimicry between human ganglioside GM1 and Campylobacter Jejuni lipooligosaccharide causes Guillain-Barre syndrome," Proc Natl Acad Sci USA, 101(31):11404-9, 2004.

Park et al., "Continuous Dielectrophoretic Bacterial Separation and Concentration from Physiological Media of High Conductivity," Lab Chip, 11:2893-2900, 2011.

Arnold et al., "Electro-Rotation: Development of a Technique for Dielectric Measurements on Individual Cells and Particles," Journal of Electrostatics, 21:151-191, 1988.

Arvin et al., "The Role of Inflammation and Cytokines in Brain Injury," Neuroscience and Biobehavioral Reviews, 20(3):445-452, 1996.

Becker et al., "Separation of Human Breast Cancer Cells from Blood by Differential Dielectric Affinity," Proc. Natl. Acad. Sci. USA, 92:860-864, Jan. 1995.

Becker et al., "The Removal of Human Leukaemia Cells for Blood Using Interdigitated Microelectrodes," J. Phys. D: Appl. Phys., 27:2659-2662, 1994.

Buzzigoli et al., "Plasmapheresis treatment in Guillain-Barre syndrome: potential benefit over intravenous immunoglobulin," Anaesth Intensive Care, 38(2):387-389, Mar. 2010.

Cambria et al., "Clinical Experience with Epidural Cooling for Spinal Cord Protection during Thoracic and Thoracoabdominal Aneurysm Repair," Journal of Vascular Surgery, 25(2):234-243, Feb. 1997.

Cook, "Combined Spinal-Epidural Techniques," Anaesthesia, 55:42-64, 2000.

Covaciu et al., "Brain Temperature in Volunteers Subjected to Intranasal Cooling," Intensive Care Med, 37(8):1277-1284, Aug. 2011.

Delhaas, "Extradural and Subarachnoid Catheterization Using the Seldinger Technique," British Journal of Anaesthesia, 76:149-150, 1996.

Elefteriades et al., "Litigation in Nontraumatic Aortic Diseases—A Tempest in the Malpractice Maelstrom," Cardiology, 109:263-272, 2008.

Enchev et al., "Historical Trends of Neuroendoscopic Surgical Techniques in the Treatment of Hydrocephalus," Neurosurgery Review, 31:249-262, 2008.

Gascoyne et al., "Dielectrophoretic Separation of Cancer Cells from Blood," IEEE Transactions of Industry Applications, 33(3):670-678, May/Jun. 1997.

Gascoyne et al., "Isolation of Rare Cells from Cell Mixtures by Dielectrophoresis," Electrophoresis, 30(8):1388-1398, 2009.

Gascoyne et al., "Particle Separation by Dielectrophoresis," Electrophoresis, 23(13):1973-1983, Jul. 2002.

Haltiwanger, "The Electrical Properties of Cancer Cells," www.royalrife.com/haltiwanger1, pp. 1-62.

Han et al., "An Electrorotation Technique for Measuring the Dielectric Properties of Cells with Simultaneous Use of Negative Quadropolar Dielectrophoresis and Electrorotation," Analyst, 138:1529-1537, 2013.

Helmy et al., "The Cytokine Response to Human Traumatic Brain Injury: Temporal Profiles and Evidence for Cerebral Parenchymal Production," Journal of Cerebral Blood Flow & Metabolism, 31:658-670, 2011.

Huang et al., "Eiectode Design for Negative Dielectrophoresis," Measurement Science and Technology, 2:1142-1146, Dec. 1991.

Jones et al., "Multipolar Dielectrophoretic and Electrorotation Theory," Journal of Electrostatics, 37:121-134, 1996.

Lau et al., "Tau Protein Phosphorylation as a Therapeutic Target in Alzheimer's Disease," Current Topics in Medicinal Chemistry, 2:395-415, 2002.

Levi et al., "Clinical Application of Modest Hypothermia After Spinal Cord Injury," J. Neurotrauma, 26(3):407-415, Mar. 2009.

Li et al., "Continuous Dielectrophoretic Cell Separation Microfluidic Device," Lab Chip, 7:239-248, 2007.

Madeira-Lopes et al., "Comparative Study of the Temperature Profiles of Growth and Death of the Pathogenic Yeast *Cryptococcus neoformans* and the non-pathogenic Cryptococcus Albidus," Journal of Basic Microbiology, 26:43-47, 1986.

Markx et al., "Dielectrophoretic Separation of Bacteria Using a Conductivity Gradient," Journal of Biotechnology, 51:175-180, Dec. 1996.

Markx et al., "Dielectrophoretic Separation of Cells: Continuous Separation," Biotechnology and Bioengineering, 45(4):337-343, Feb. 1995.

Marszalek et al., "Determination of Electric Parameters of Cell Membranes by a Dielectrophoresis Method," Biophysical Journal, 59:982-987, May 1991.

Mckeating et al., "Cytokines and Adhesion Molecules in Acute Brain Injury," British Journal of Anaesthesia, 80:77-84, 1998.

Misaki et al., "Contrast-Enhanced Fluid-Attenuated Inversion Recovery MRI is Useful to Detect the CSF Dissemination of Glioblastoma," Journal of Computer Assisted Tomography, 25(6):953-956, 2001.

Morganti-Kossman et al., "Production of Cytokines Following Brain Injury: Beneficial and Deleterious for the Damaged Tissue," Molecular Psychiatry, 2:133-136, 1997.

Onda, et al., "Cerebral Glioblastoma with Cerebrospinal Fluid Dissemination: A Clinicopathological Study of 14 Cases Examined by Complete Autopsy," Neurosurgery, 25(4):533-540, 1989.

Park et al., "3-D Electrode Designs for Flow-Through Dielectrophoretic Systems," Electrophoresis, 26:3745-3757, 2005.

Perfect, "Cryptococcus Neoformans:The Yeast that Likes it Hot," FEMS Yeast Res., 6:463-468, 2006.

Pethig et al., "Applicants of Dielectrophoresis in Biotechnology," Tibtech, 15:426-432, Oct. 1997.

Pethig, "Dielectrophoresis: Status of the Theory, Technology, and Applications," Biomicrofluidics, 4:022811-1-022811-35, 2010.

Pethig, "Dielectrophoresis: Using Inhomogeneous AC Electrical Fields to Separate and Manipulate Cells," Critical Reviews in Biotechnology, 16(4):331-348, Sep. 2008.

Polderman et al., "Therapeutic Hypothermia and Controlled Normothermia in the Intensive Care Unit: Practical Considerations, Side Effects, and Cooling Methods," Crit. Care Med., 37(3):1101-1120, Mar. 2009.

Reiber, "Proteins in cerebrospinal fluid and blood: Barriers, CSF flow rate and source-related dynamics," Restorative Neurology and Neuroscience, 21:79-96, 2003.

Stephens et al., "The Dielectrophoresis Enrichment of CD34 Cells from Peripheral Blood Stem Cell Harvests," Bone Marrow Transplantation, 18:777-782, 1996.

Tay et al., "Electrical and Thermal Characterization of a Dielectrophoretic Chip with 3D Electrodes for Cells Manipulation," Electrochimica Acta, 52:2862-2868, 2007.

"External CSF Drainage," Aqueduct Neurosciences, 2 pages, Jul. 2014.

"Therapeutic Hypothermia for Spinal Cord Injury," Crit. Care Med., 37:S238-S242, Jul. 2009.

Liquoguard, "Moiler Medical", Brochure, 2 pages.

World Journal of Radiology, 4(6):241-290, Jun. 28, 2012.

Voldman, "Electrical Forces for Microscale Cell Manipulation," Annu. Rev. Biomed. Eng., 8:425-454, 2006.

(56)  References Cited

OTHER PUBLICATIONS

Weis et al., "Noninvasive Monitoring of Brain Temperature During Mild Hypothermia," Magn. Reson. Imaging, 27(7):923-932, Sep. 2009.

Ziebell et al., "Involvement of Pro- and Anti-Inflammatory Cytokines and Chemokines in the Pathophysiology of Traumatic Brain Injury," The Journal of the American Society for Experimental Neuro Therapeutics, 7:22-30, Jan. 2010.

Siddiqui et al., "Use of the Penumbra System 054 plus Low Dose Thrombolytic Infusion for Multifocal Venous Sinus Thrombosis," Interventional Neuroradiology, 18:314-319, 2012.

Spiegelberg, "EVD-Catheters," website, http://www.spiegelberg.de/products/drainage/silverline_evd_catheter_3001002.html, 1 page, downloaded Nov. 3, 2016.

Wagner et al., "Ultra-early clot aspiration after lysis with tissue plasminogen activator in a porcine model of intracerebral hemorrhage: edema reduction and blood-brain barrier protection," J. Neurosurg., 90:491-498, Mar. 1999.

Ziu et al., "A Series of Cerebral Venous Sinus Thromboses Treated with Intra-Arterial tPA infused over Ten Hours with a 0.027-inch Catheter and Literature Review," pp. 1-13, Jun. 23, 2016.

Blumenfeld, "Neuroanatomy through Clinical Cases," 2002.

International Search Report and Written Opinion of the International Searching Authority dated Sep. 8, 2016 for International Patent Application No. PCT/US2016/036626.

Office Action dated Apr. 26, 2017 from Japanese Patent Application No. 2016-131320.

Office Action dated Apr. 26, 2017 from Japanese Patent Application No. 2016-131321.

* cited by examiner

Figure 5.11 Brain Ventricles A) Ventricles viewed from lateral surface of brain. B) Ventricles viewed from anterior surface of brain. C) Ventricles viewed from superior surface of brain. D) Details of ventricular structure.

Model of brain and spinal column
illustrating single-lumen lumbar approach
for CSF access:
-Creates a local eddy.
-Poor mixing.
-Inefficient.
-Significant turnover of same/previously
processed CSF.
-Limited significantly by pressure/volume
dynamics.
-Requires sequential CSF processing.

*Figure 8A*

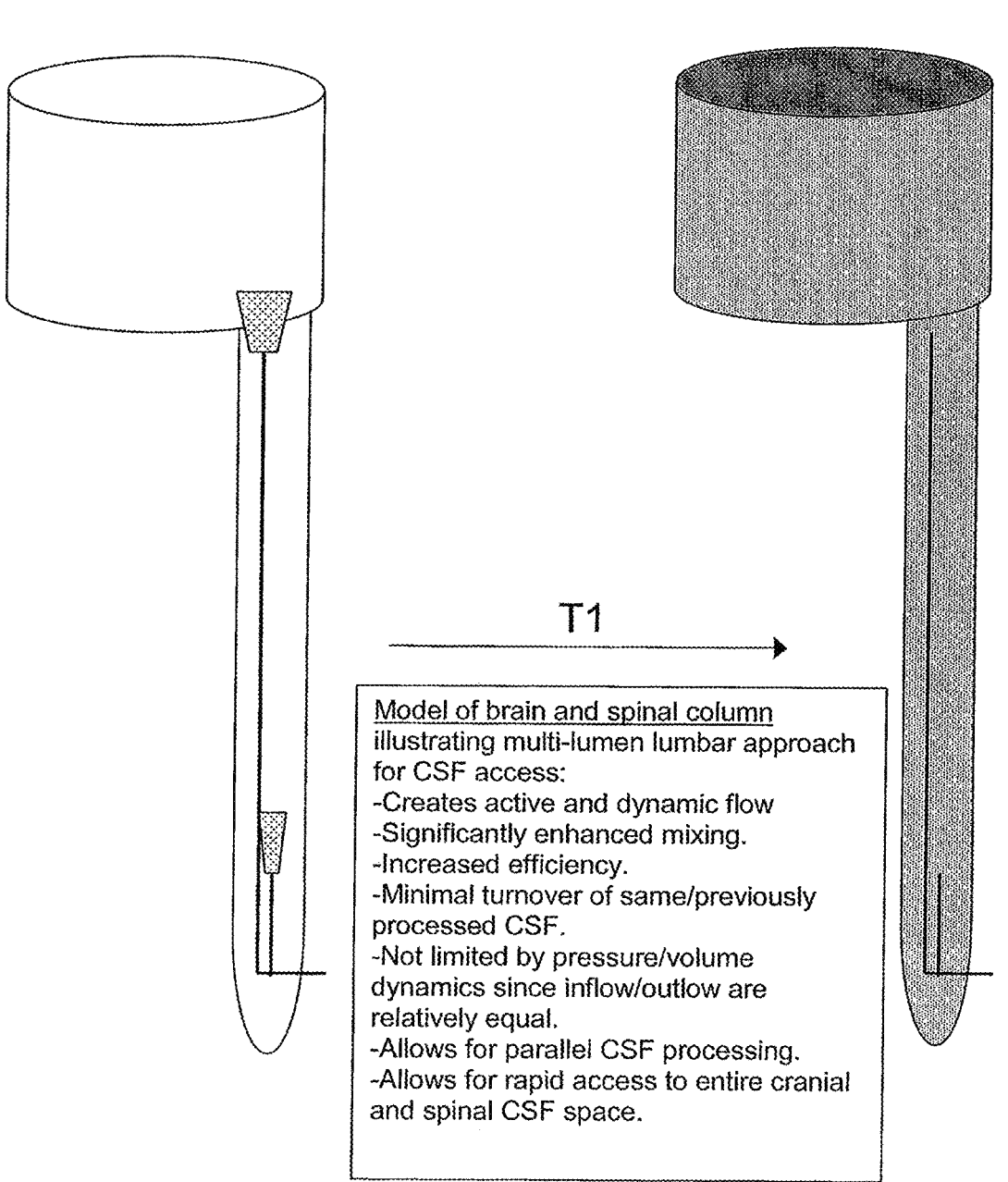

T1

Model of brain and spinal column
illustrating multi-lumen lumbar approach
for CSF access:
-Creates active and dynamic flow
-Significantly enhanced mixing.
-Increased efficiency.
-Minimal turnover of same/previously
processed CSF.
-Not limited by pressure/volume
dynamics since inflow/outlow are
relatively equal.
-Allows for parallel CSF processing.
-Allows for rapid access to entire cranial
and spinal CSF space.

*Figure 8B*

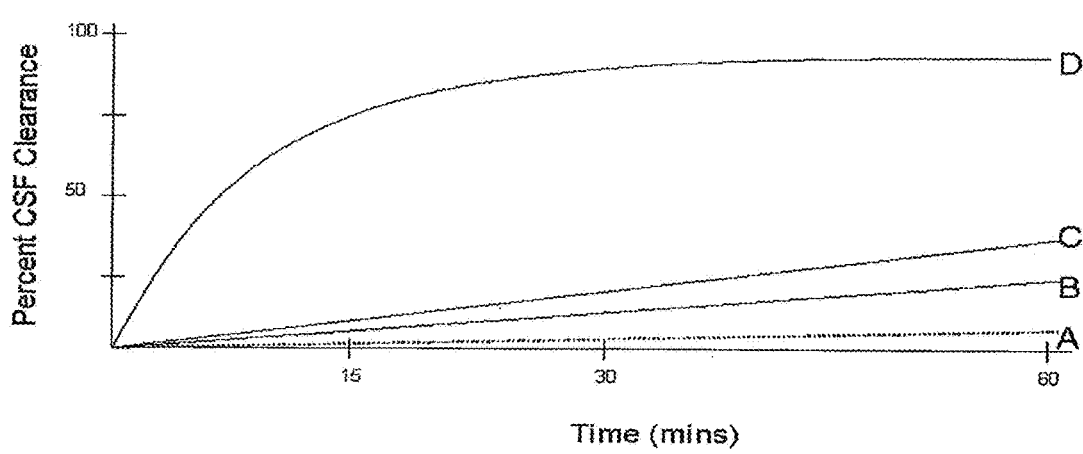

A= Diffusion
B= Single lumen catheter
C= Multilumen catheter with inflow/outflow directly adjacent
D= Multilumen catheter with inflow/out sufficient to create efficient CSF mixing

*Figure 8C*

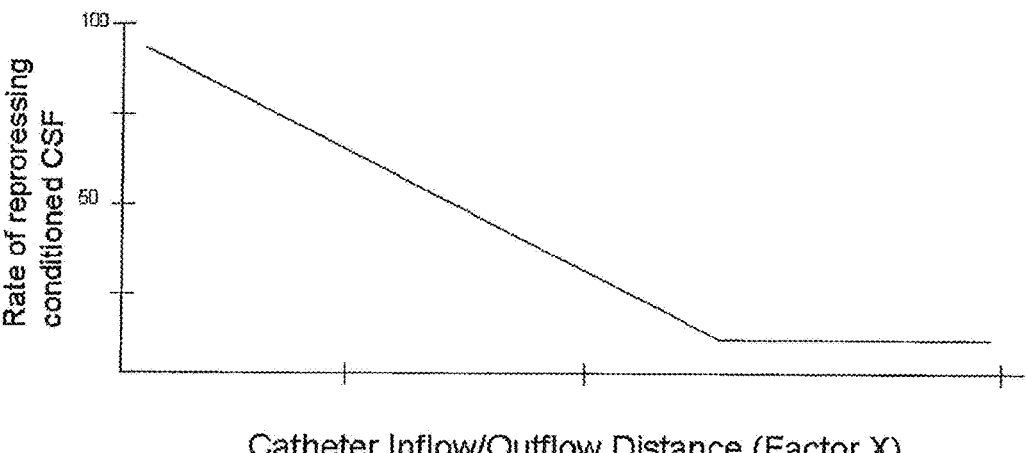

Factor X is based on a number factors and is largely related to
size of separation based on distance between inflow and outflow,
however can also be affected by a number of other factors including size,
direction, flow rate, temperature, patient angle, gravity, number of lumens.

ADDRESSABLE SIDE PARTS

CEREBROSPINAL FLUID PURIFICATION SYSTEM

CROSS-REFERENCES TO RELATED APPLICATIONS

The present application is a continuation of U.S. patent application Ser. No. 16/548,554, filed Aug. 22, 2019; which is a continuation of U.S. patent application Ser. No. 15/410, 219, filed Jan. 19, 2017, now U.S. Pat. No. 10,398,884; which is a continuation of U.S. patent application Ser. No. 13/801,215, filed Mar. 13, 2013, now U.S. Pat. No. 9,895, 518; which is a continuation of U.S. patent application Ser. No. 12/444,581, filed Jul. 1, 2010, now U.S. Pat. No. 8,435,204; which is the U.S. National Phase entry of International Patent Application No. PCT/US2007/080834, filed Oct. 9, 2007, which claims the benefit of U.S. Provisional Application No. 60/828,745, filed Oct. 9, 2006. The entireties of the above-captioned applications are incorporated by reference herein for all purposes.

FIELD OF THE INVENTION

The invention pertains generally to medical devices and methods. More particularly, the present invention relates to devices, systems methods and kits for removal of toxins from the cerebrospinal fluid (CSF). More specifically, the method and system can be used to diagnose and treat disorders affecting the central nervous system (CNS) by measuring and modifying the chemical composition of CSF.

BACKGROUND OF THE INVENTION

Others have described devices for the handling and/or removal of cerebrospinal fluid (CSF) to and from a patient.

For example, several patents disclose various methods for diverting or shunting CSF from the CSF space (ventricle, spinal column) to another portion of the body (e.g., abdomen, peritoneal cavity). See, e.g., U.S. Pat. Nos. 2,969,066; 3,889,687; 6,575,928 and 7,118,549. Others have described administering therapeutic agents to the CSF space, but do not disclose removing the CSF. See, e.g., U.S. Pat. Nos. 5,531,673; 6,056,725; 6,594,880; 6,682,508 and 6,689,756. Generally, the therapeutic agents are locally delivered to the brain but not to the greater cerebrospinal fluid space, which includes the brain and the spine. Others disclose removing CSF, but generally do not administer therapeutic agent or any other fluid. See, e.g.; U.S. Pat. Nos. 3,889,687; 5,683, 357; 5,405,316 and 7,252,659.

Devices exist having both input and output catheters for administering therapeutic agents or synthetic CSF and removing endogenous CSF, but the close spatial placement of the inflow and outflow catheters do not allow for flow of CSF throughout the cerebrospinal fluid space or full CSF exchange that provides access to the complete intracranial and intraspinal CSF volume. See, e.g., U.S. Pat. Nos. 4,378,797; 4,904,237; 6,537,241 and 6,709,426.

Furthermore, publications disclosing the exchange of CSF describe replacing endogenous CSF with synthetic CSF replacement fluid. See, e.g., U.S. Patent Publication No. 2003/0065309; and PCT Publication Nos. WO 01/154766 and WO 03/015710. In this way, the concentration of the toxic species may be diluted but not removed. It has been proposed to treat drug overdose or removal of tumor cells to clear debris before implantation of a ventriculo-peritoneal shunt shunt system. Such an apparatus is unnatural in that it requires flushing the entire system with an artificially produced solution rather than removing the toxins of interest from the patient's endogenous CSF, requires liters of instilled replacement fluid to be delivered on a regular basis, is neither targeted nor focused for removal of specific toxins of interest and is only practical in an acute setting where liters of fluid could be instilled. See, e.g. PCT Publication No. WO 01/54766.

Various devices aimed at accessing the CSF or indirectly targeting the nervous system exist, however there exists no CSF purification system that allows for the direct, targeted, logical and disease-specific removal of one or more of target compounds or the use of a dual or multi-lumen catheter that influences or controls CSF flow, mixing and efficiency of turnover.

It is desirable to provide a method and system for processing and removal of one or more target compounds from the CSF of a patient. Recently, a treatment for Alzheimer's disease was suggested which relied on removal of CSF by diversion of the fluid from the brain (ventricular system) to another portion of the patients body (e.g. abdomen/peritoneal cavity) using a modified ventriculo-peritoneal shunt system. See, e.g., U.S. Pat. Nos. 5,980,480 and 7,025,742. By continuously draining CSF at a low rate, the rationale was that the body's daily production of new CSF would dilute the concentration of contaminating substances remaining in the endogenous CSF. Such a system has several inherent limitations. The rate at which the concentration of toxic species is lowered is mediated by passive flow, is very slow, addresses only a fraction (milliliters) of the total CSF volume per hour, is not targeted or focused in removing specific items of interest and does not prevent reabsorption of toxic species back into the systemic circulation and thereby back into the CSF. See, e.g. U.S. Pat. Nos. 5,980, 480; 6,264,625; 6,689,085.

The present invention addresses this and other needs.

BRIEF SUMMARY OF THE INVENTION

The present invention provides systems and methods for conditioning cerebrospinal fluid (CSF).

Accordingly, in a first aspect, the invention provides methods for conditioning cerebrospinal fluid (CSF) in a patient. In some embodiments, the methods comprise:

a) removing CSF from a first location in a CSF space of the patient;

b) conditioning the removed CSF; and c) returning the conditioned CSF to the patient at a second location in the CSF space; wherein the removing and returning steps are performed concurrently during at least a portion of a conditioning treatment.

In another aspect, the invention provides methods for conditioning cerebrospinal fluid (CSF) in a patient, the methods comprising:

a) introducing a catheter apparatus through a spinal (e.g., sacral, lumbar, thoracic, cervical) access site into the spinal CSF space of a patient;

b) advancing the catheter apparatus through the spinal CSF space cranially (toward the brain) such that a distal port and a proximal port on the catheter apparatus are disposed within the CSF space and spaced-apart by a preselected distance;

c) withdrawing CSF through one of said ports;

d) conditioning the withdrawn CSF; and e) returning the conditioned CSF through the other of said ports.

In another aspect, the invention provides methods for conditioning cerebrospinal fluid (CSF) in a patient, the methods comprising:

a) introducing a catheter apparatus into a brain ventricle or into the subarachnoid space of a patient;

b) advancing the catheter apparatus into the spinal CSF space such that a distal port and a proximal port on the catheter apparatus are disposed within the CSF space and spaced-apart by a preselected distance;

c) withdrawing CSF through one of said ports;

d) conditioning the withdrawn CSF; and e) returning the conditioned CSF through the other of said ports.

In another aspect, the invention provides methods for conditioning cerebrospinal fluid in a patient, the methods comprising:

a) introducing a catheter apparatus into a brain ventricle of a patient;

b) adjusting spacing between a pair of ports on the catheter apparatus so one port lies on one side of the ventricle and the other port lies on another side of the ventricle;

c) withdrawing CSF through one of said ports;

d) conditioning the withdrawn CSF; and e) returning the conditioned CSF to the ventricle through the other of said ports.

With respect to the embodiments of the methods, in some embodiments, the CSF is removed or withdrawn and returned at substantially the same flow rate. In some embodiments, the CSF is removed or withdrawn and returned at the same flow rate. In some embodiments, the flow rate is in the range from about 0.04 ml/min to about 30 ml/min, for example, from about 5 ml/min to about 20 ml/min, for example, about 1, 2, 3, 5, 7, 10, 12, 15, 18 or 20 ml/min.

In some embodiments, the volume of CSF removed is below the volume that would induce a spinal headache or symptoms of overdrainage. In some embodiments, the volume of CSF removed from the patient never exceeds about 35-45 ml, for example, about 40 ml, 35 ml, 30 ml or 25 ml.

In some embodiments, the distance between the first location and the second location is at least about 4 cm, for example, about 5, 10, 20, 25, 30, 35, 40, 45, 50, 55, 60, 70, 80, 90 or 100 cm. In some embodiments, the distance between the first location and the second location is separated by at least about 2 vertebrae.

In some embodiments, the first location or the proximal port is at sacral Si or lumbar L5 or above and the second location is at lumbar L3 or above. In some embodiments, the first location or proximal port is at S1, L5, L4, L3, L2, L1 or above. In some embodiments, the second location or distal port is in the sacral, lumbar, thoracic or cervical CSF space. In some embodiments, the second location or distal port is in one or more ventricles. In some embodiments, the second location or distal port is in the cranial subarachnoid space.

In some embodiments, the first location or proximal port is in the cranial subarachnoid space. In some embodiments, the first location or proximal port is in one or more ventricles. In some embodiments, the second location or distal port is in the lumbar, thoracic or cervical CSF space. In some embodiments, the second location or distal port is in the lumbar CSF space, for example at S1, L5, L4, L3, L2, L1 or above.

In some embodiments, the first location or proximal port and the second location or distal port is in the ventricular space. For example, both the first location or proximal port and the second location or distal port can on opposite sides of one ventricle. In another example, the first location or proximal port is in a first ventricle and the second location or distal port is in a second ventricle.

In some embodiments, the distance between the first location or proximal port and the second location or distal port is adjustable. For example, a pair of tubular members in a multilumen catheter can be axially adjusted relative to one another.

In some embodiments, the flow directions of removing or withdrawing and returning CSF are periodically reversed so that CSF is returned to the first location and removed from a second location during a portion of the treatment. For example, the flow reversal is a pulse to dislodge debris from removal or return ports.

In some embodiments, the methods further comprise the step of mixing the conditioned CSF with unconditioned CSF as the conditioned CSF is returned to the CSF space. In some embodiments, the methods comprise inducing a turbulent flow as the conditioned CSF is returned which enhances mixing. For example, the turbulent flow can be created by introducing a multilumen catheter comprising one or more helical flow paths, textured (e.g., ribbed or bumped) flow paths, a T-separated flow path, bellows, balloons, fins, and/or multiple exit ports (e.g., side holes or side vents). Turbulent flow can also be induced by high pressure injection (i.e., "jetting") or directed outflow.

In some embodiments, the conditioning comprises removing a targeted molecule (e.g., protein, peptide, oligopeptide) from the CSF. For example, the conditioning can comprise one or more separation processes selected from the group consisting of biospecific affinity (e.g., antibodies, nucleic acids, receptors, enzymes), immunoaffinity, cationic exchange, anionic exchange, hydrophobicity and various size exclusion thresholds.

In some embodiments, the methods further comprise the step of isolating the targeted molecule.

In some embodiments, the conditioning comprises removing pathological cells (e.g., B-cell, T-cells, macrophages, erythrocytes and other blood cells) and cellular debris.

In some embodiments, the conditioning step is performed externally to the patient's body. In some embodiments, the conditioning step is performed using a conditioning unit implanted in the patient's body.

In some embodiments, the catheter apparatus consists essentially of a single catheter body having a lumen connected to the distal port and a separate lumen connected to the proximal port.

In some embodiments, the methods comprise ameliorating the symptoms of Alzheimer's Disease in a patient by removing at least one of beta-amyloid or tau proteins from CSF employing the methods and systems described above and herein.

In some embodiments, the methods comprise ameliorating the symptoms of Parkinson's Disease in a patient by removing at least one of alpha-synuclein proteins (including peptides or oligomers) from CSF employing the methods and systems described above and herein.

In some embodiments, the methods comprise ameliorating the symptoms of Amyotrophic Lateral Sclerosis (ALS) in a patient by removing at least one of insoluble superoxide dismutase-1 (SOD1), glutamate, neurofilament protein, and anti-GM1 ganglioside antibodies from CSF employing the methods and systems described above and herein.

In some embodiments, the methods comprise ameliorating the symptoms of cerebral vasospasm in a patient by removing at least one of blood cells (e.g., erythrocytes), oxyhemoglobin and endothelin from CSF employing the methods and systems described above and herein.

In some embodiments, the methods comprise ameliorating the symptoms of encephalitis in a patient by removing at least one of the causative bacterial or viral entity, tumor necrosis factor-alpha (TNFa) and IgG from CSF employing the methods and systems described above and herein.

In some embodiments, the methods comprise ameliorating the symptoms of Guillain Barre Syndrome (GB S) in a patient by removing at least one of cells and inflammatory mediators including but not limited to C5a, TNF a, IL 2, IL-6, interferon-y, IgG, and endotoxins from CSF employing the methods and systems described above and herein.

In some embodiments, the methods comprise ameliorating the symptoms of Multiple Sclerosis (MS) in a patient by removing at least one of T cells, B cells, anti-myelin antibodies and inflammatory mediators including but not limited to TNF a, IL 2, IL-6, interferon-y from CSF employing the methods and systems described above and herein.

In some embodiments, the methods comprise ameliorating the symptoms of stroke in a patient by removing inflammatory mediators including but not limited to endothelin and enolase and cooling the CSF (and hence the CNS), employing the methods and systems described above and herein.

In a related aspect, the methods provide systems for conditioning cerebrospinal fluid (CSF) in a patient. In some embodiments, the systems comprise i) a catheter assembly having a first lumen with a distal port and a second lumen with a proximal port, said catheter being adapted to be introduced in a CSF space and said ports being spaced axially apart;

ii) a pump connectable between the first and second lumens to induce a flow of CSF therebetween; and iii) a conditioning component connectable between the first and second lumens to condition the CSF flowing therebetween.

With respect to the embodiments of the systems, in some embodiments, the catheter assembly consists essentially of a single tubular member having the first lumen and distal port and the second lumen and proximal port fixedly disposed therein.

In some embodiments, the catheter comprises a first tubular member having the first lumen and the distal port therein and a second tubular member having the second lumen and proximal port therein.

In some embodiments, the first and second tubes can be axially translated relative to each other to adjust the distance therebetween.

In some embodiments, the pump has a flow rate adjustable between about 0.04 ml/min to about 30 ml/min, for example, from about 5 ml/min to about 20 ml/min, for example, about 1, 2, 3, 5, 7, 10, 12, 15, 18 or 20 ml/min. In some embodiments, the pump comprises a peristaltic pump which is isolated from the CSF flow. In some embodiments, the pump is implantable (e.g., an Archimedes screw).

In some embodiments, the conditioning component is selected from the group consisting of biospecific affinity, immunoaffinity, cationic exchange, anionic exchange, hydrophobicity and size exclusion. For example, the conditioning component can be a column or a cartridge. In some embodiments, the catheter comprises the conditioning component (e.g., bound to the inner surface of the catheter by covalent or non-covalent bonding).

With respect to size exclusion and filtration, the filtration component can be any type, e.g., membranous, nanoparticular, flat, tubular or capillary.

In some embodiments, the system has a CSF retention volume below about 40 ml, for example, below about 35, 30, 25 or 20 ml.

In some embodiments, the system is implantable. In some embodiments, the system is partially external.

Definitions

The term "patient" refers to any mammal. The mammal can be a non-human mammal, a non-human primate or a human. In some embodiments, the mammal is a domestic animal (e.g., canine, feline, rodentia, etc.), an agricultural mammal (e.g., bovine, ovine, equine, porcine) or a laboratory mammal (rodentia, rattus, murine, lagomorpha, hamster).

The term "CSF space" refers to any volume of cerebrospinal fluid found in the cranial or spinal areas that is in contact with any component of the nervous system, but not within the tissue. Interstitial fluid resides in the tissue.

The phrase "conditioning CSF" or "conditioned CSF" interchangeably refer to CSF wherein one or more target compounds have been partially, mostly or entirely removed.

The phrase "consisting essentially of refers to the elements recited in the claim as well as insubstantial elements, and excludes elements that materially change the invention.

BRIEF DESCRIPTION OF THE DRAWINGS

Figure 6A:
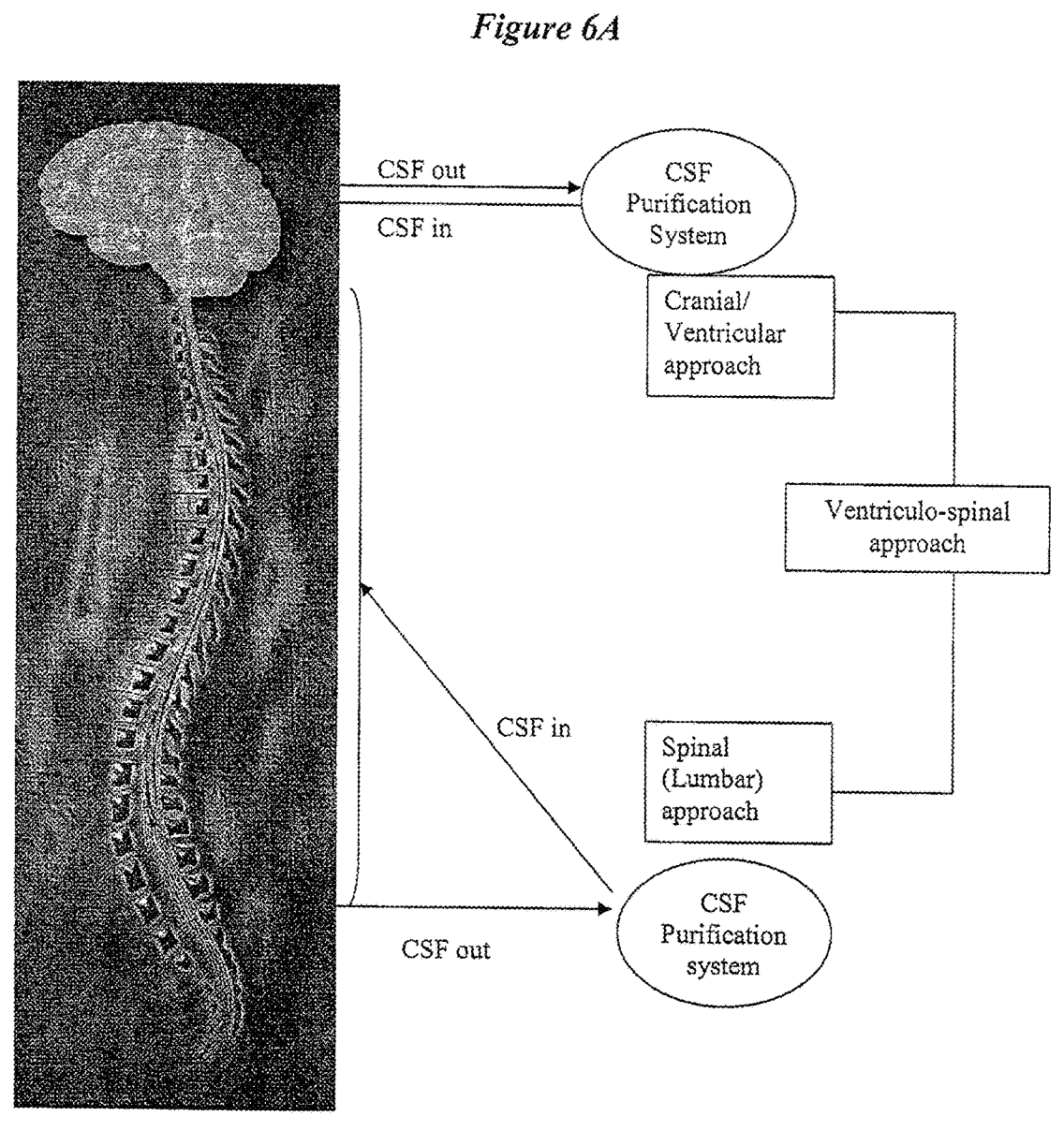

FIG. 6A illustrates a schematic of the ventricular, spinal and ventriculo-spinal approaches for accessing the CSF space for the efficient turnover of conditioned CSF.

FIG. 8A illustrates a schematic of a dual lumen system of the invention. A multi-lumen system creates an active and dynamic flow with efficient mixing that is not limited by pressure volume as inflow and outflow are relatively equal. This allows for parallel processing of CSF with maximum turnover and provides access to the cranial and spinal space and entire CSF volume (mixing represented by shading). FIG. 8B illustrates the dramatic difference in CSF clearance produced with a multilumen system in which inflow and outflow are substantially apart (line D), adjacent (line C) compared to a single lumen system (line B) compared to diffusion-limited flow (line A). FIG. 8C illustrates the effect of catheter inflow/outflow distance on the rate of reprocessing of conditioned CSF.

FIG. 10A illustrates a single helical outflow path over last length (l) of catheter. A straight outflow lumen connects to the helical path. The catheter comprises a straight central inflow lumen. FIG. 10B illustrates a dual helical outflow path catheter with central inflow path.

DETAILED DESCRIPTION OF THE INVENTION

1. Introduction

The present invention provides methods, devices and systems for removing, detecting, returning and delivering compounds from and/or to a patient's cerebrospinal fluid (CSF) space. The removal and/or delivery of specific compounds can be tailored to the pathology of the specific disease. The removal is targeted and specific, for example, through the use of specific size-exclusion thresholds, antibodies against specific toxins, and other chromatographic techniques, as well as delivery and/or removal of targeted therapeutic agents. The invention finds use as a diagnostic, therapeutic and drug delivery platform for a variety of diseases affecting the CNS by accessing the CSF space.

For the first time, the present invention offers a targeted, focused and logical treatment platform to treat a variety of debilitating and often devastating neurological diseases to which there are presently limited and ineffective treatment options. Exemplified disease conditions treatable by the present CSF processing systems and methods include, but are not limited to: Cerebral Vasospasm, Guillain Bane Syndrome, Alzheimer's, Parkinson's, Huntington's, Multiple Sclerosis, Amyotrophic Lateral sclerosis, Spinal Cord Injury, Traumatic Brain Injury, Stroke, Cancer affecting the brain or spinal cord, Prion disease, Encephalitis from various causes, Meningitis from various causes, diseases secondary to enzymatic or metabolic imbalances, Biological Warfare, etc. For the first time, the present invention offers patients a disease-modifying, disruptive technology that addresses the known disease pathogenesis and effectively ameliorates the symptoms of a number of neurologic conditions.

Figure 1:
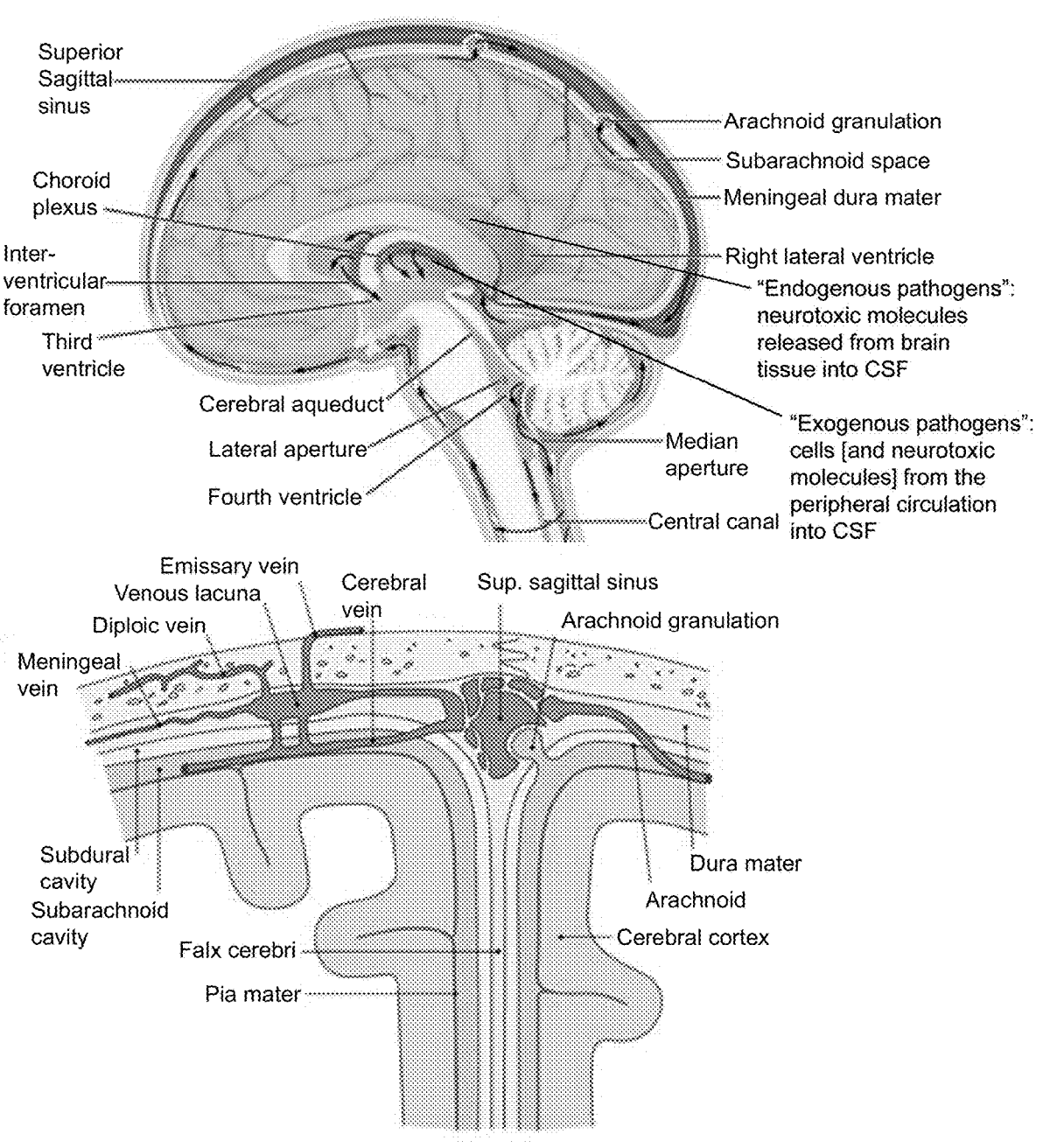
FIG. 1 illustrates a sagittal cross-section through the brain and spinal cord and illustrates the location of the choroid plexus and the passive flow of CSF through the CNS. The inset depicts the arachnid granulations located along the major venous sinuses, which are the primary locations for CSF reabsorption.

CSF: Cerebrospinal fluid (CSF) is primarily produced by the human CNS by vascular plexuses termed choroid plexus in the lateral third, and fourth, ventricles of the brain (FIG. 1). This normally clear, watery fluid maintains a gradient between it and the interstitial fluid of the nervous system. Water and soluble substances are freely exchangeable between the CSF and the nervous system. Thus, many neurotransmitters, peptides and other neuroactive substances can be found within the CSF. The functional role of many of these peptides is under current research. The concentration of various neuroactive substances in the CSF is of great interest, because it represents an indirect view that corresponds closely to the extracellular fluid in the immediate vicinity of the neurons in the brain and spinal cord. Thus, CSF serves two main functions: 1) by coating the brain and spinal cord it provides a protective function, providing buoyancy and preventing traction on vessels and nerves upon impact to the skull or spinal column; 2) perhaps even more importantly, it contributes the maintenance of a constant composition of the neuronal environment. See, Blumenfeld, H. (2002). "Neuroanatomy through Clinical Cases." 951.

Figures 2A, 2B, 2C, 2D:
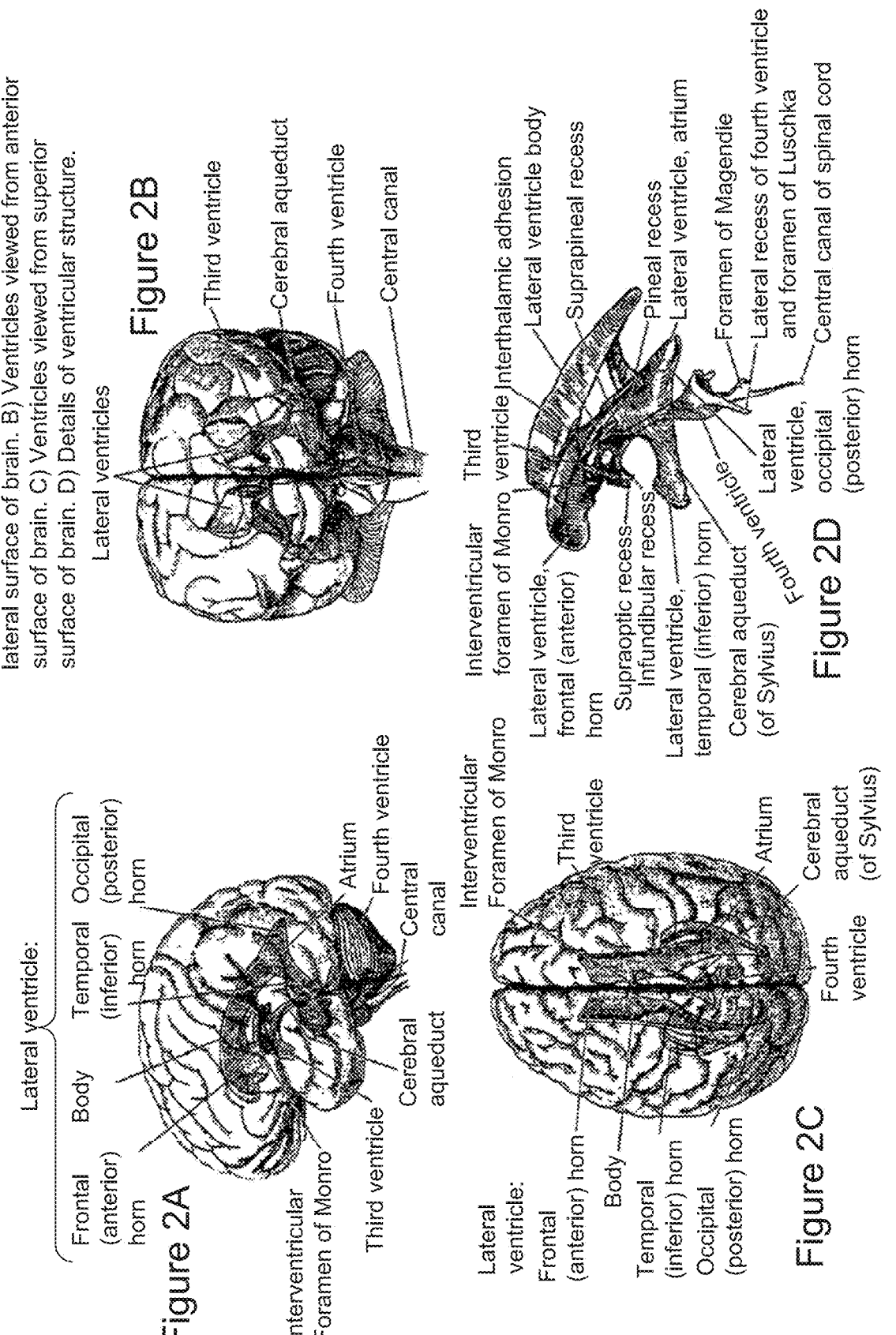
FIGS. 2A, 2B, 2C, and 2D provide views of the ventricular system from the A) lateral surface, B) anterior surface, C) superior surface and D) detailed ventricular structure.
Figure 3:
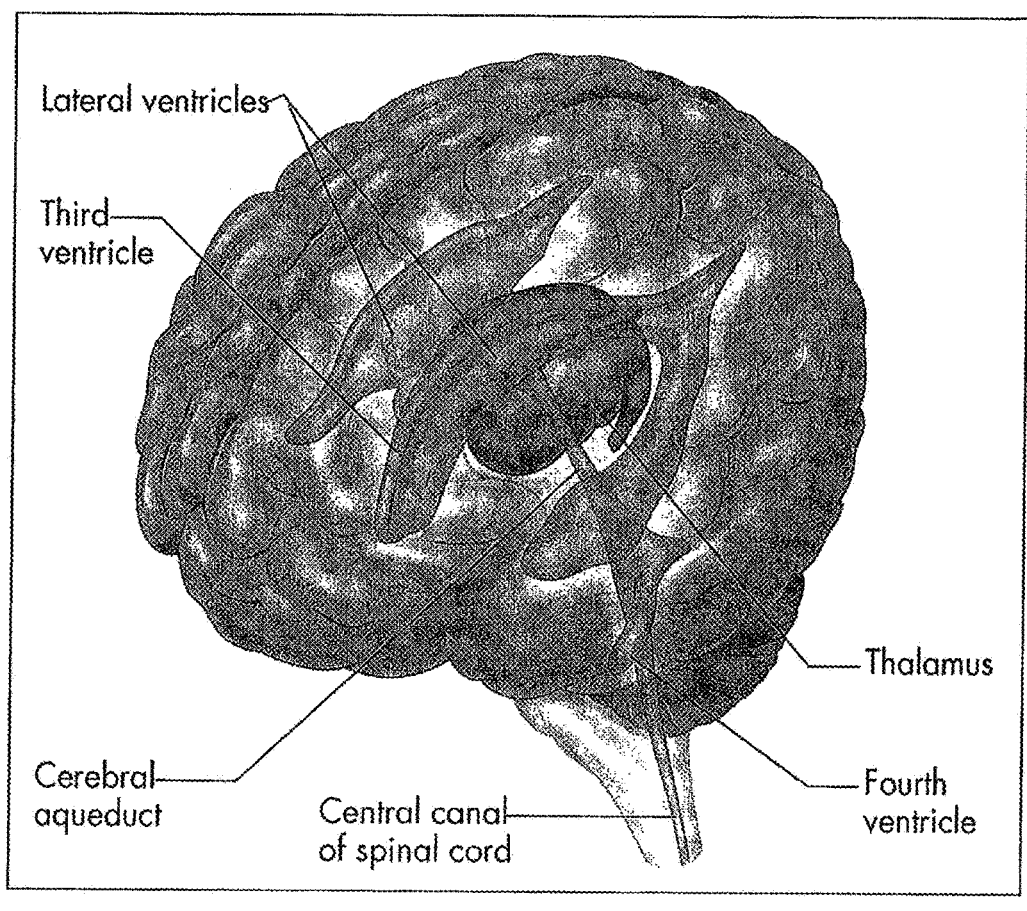
FIG. 3 illustrates the ventricular anatomy of the brain in a 3 dimensional perspective.
Figures 4A, 4B, 4C, 4D:
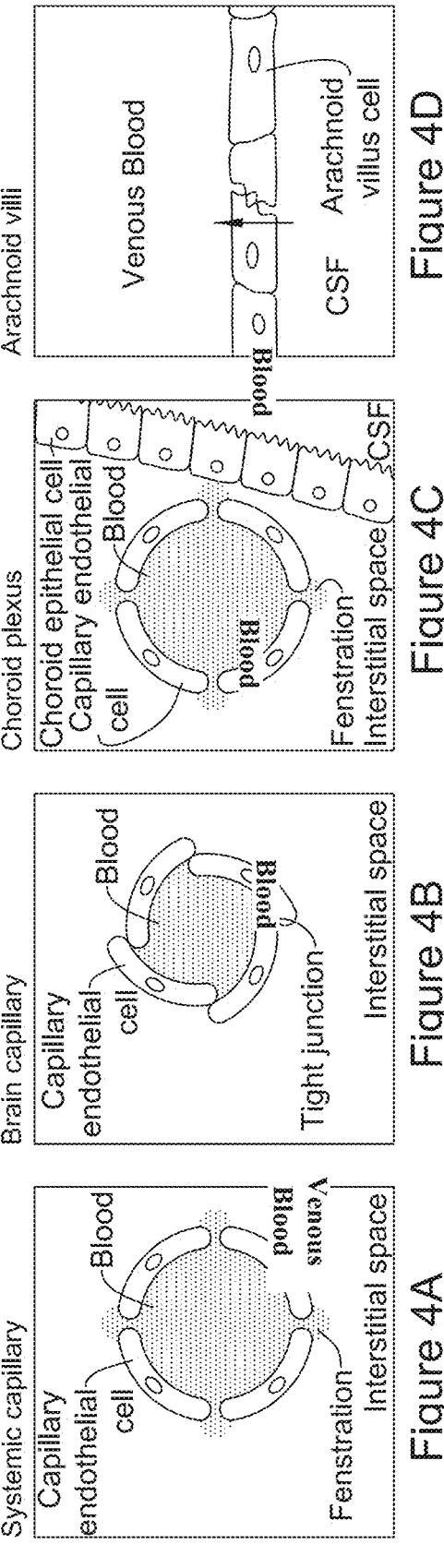
FIGS. 4A, 4B, 4C, and 4D depict the Blood-Brain and Blood-CSF Barriers. A) fenestrated capillary allowing passage of water and solutes, B) brain capillaries with tight junctions between endothelial cells, forming blood-brain barrier; requires cellular transport, C) choroids plexus epithelial cells form the blood-CSF barrier and allow water and solutes but require cellular transport, D) arachnid villi allow one-way bulk flow of CSF into major venous sinuses.

Neuroanatomy/Flow: In healthy adults, CSF is produced at a rate of about 0.3 ml/min, 18 ml/hour, or about 432 ml/day. However, the total volume found in the ventricles and subarachnoid space is about 150 ml (FIGS. 2A-2D). Thus, the total volume of CSF is turned over several (approximately three) times each day. The fluid produced in the lateral ventricles flows via the intraventricular foramen (of Monroe) into the third ventricle, then via the narrow cerebral aqueduct into the fourth ventricle (FIG. 3). From there, it exits via the midline posteriorly (foramen of Magendie) or laterally (foramen of Luschka) (FIG. 2D). The CSF then spreads over the entire surface of the brain and spinal cord, providing a constant balance of extracellular fluid to individual neurons throughout the CNS. The CSF is drained by small protrusions called arachnid granulations, which are particularly prominent along the major venous drainage sites such as the superior sagittal sinus (FIG. 1, inset). Fluid passes from the subarachnoid space to the venous sinuses by a hydrostatic gradient. Some of the CSF is also drained via other routes, such as lymphatic vessels along cranial and spinal nerves. See, Blumenfeld, H. (2002). "Neuroanatomy through Clinical Cases." 951.

Barriers: In most organs, small-molecular weight substances pass the capillary wall with relative ease, and their concentration is therefore similar in the plasma as in the interstitial (extracellular) fluid. The composition of the interstitial fluid of the CNS differs from most other organs because of the selective properties of brain capillaries, known as the blood-brain barrier (BBB). This barrier is comprised of extensive tight junctions between endothelial cells, preventing the passage of a number of substances from the peripheral plasma (FIGS. 4A-4D). Similar to the BBB, ery that several of the disorders have common underlying disease mechanisms. This provides an opportunity for intervention with a device platform that addresses a number of different diseases based on a few fundamental concepts involving the purification and modification of CSF based on size, biologic components and temperature.

It is now understood that a number of "endogenous pathogens" (neurotoxic molecules released from the brain into the CSF) and "exogenous pathogens" (cells and neurotoxic molecules from the peripheral circulation which enter the CSF) can perturb the normal environment of the CNS and are thought to play a key role in a number of diseases affecting the nervous system. See, Caughey, B. and P. T. Lansbury (2003). Annu Rev Neurosci 26: 267-98.

Figure 5:
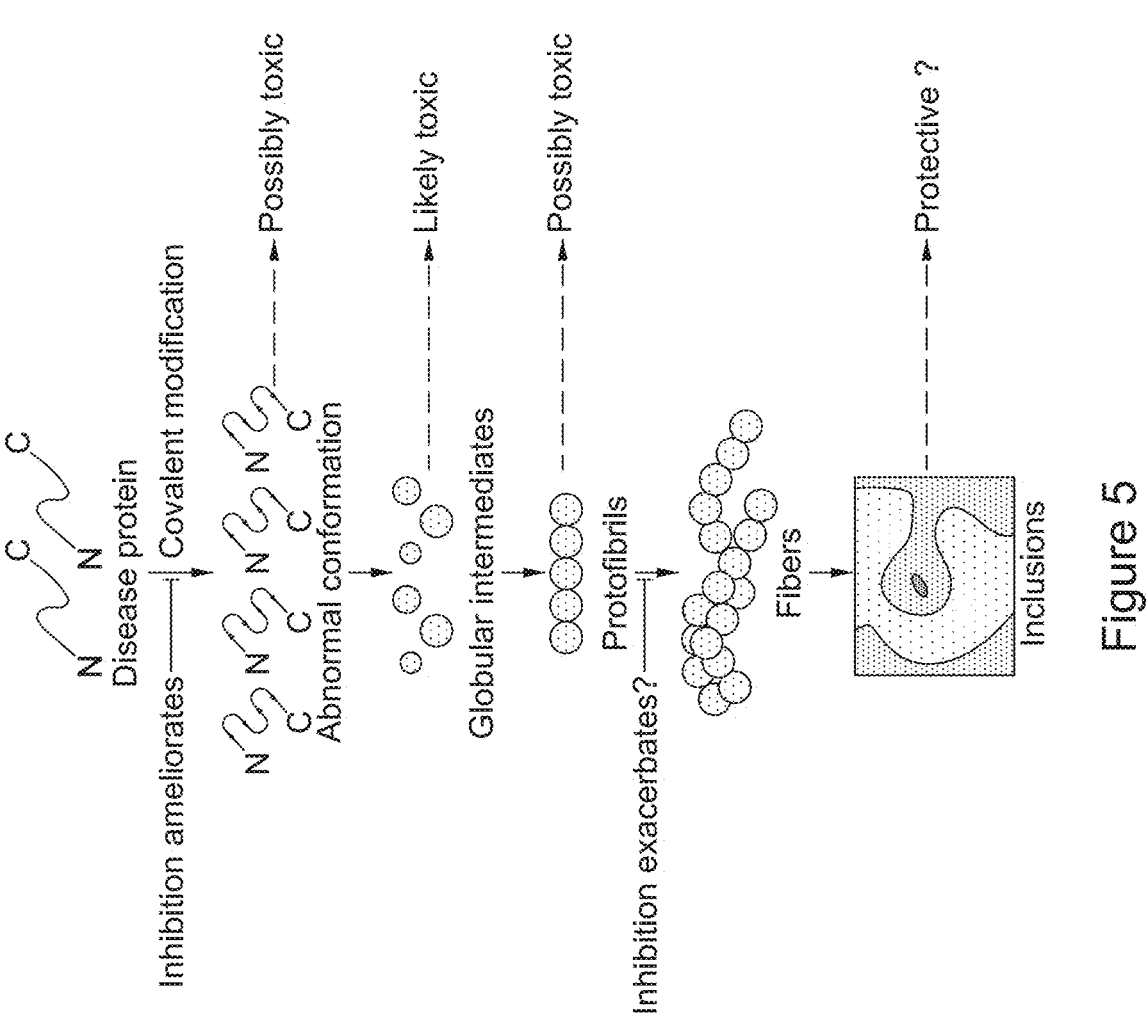
FIG. 5 illustrates the oligomeric hypothesis of neurodegenerative diseases. The multi-step process is thought to underlie a number of different neurologic conditions. The disease specific proteins undergo a specific biochemical modification which makes them prone to join and form globular intermediates (known as oligomers). These oligomers are thought to be toxic and can continue to build on one another forming protofibrils and fibrils. The fibrils may then be isolated into an intracellular inclusion (e.g. tau tangles) or an extracellular deposit (e.g. AP plaque) in the case of Alzheimer's disease.
Figure 6B:
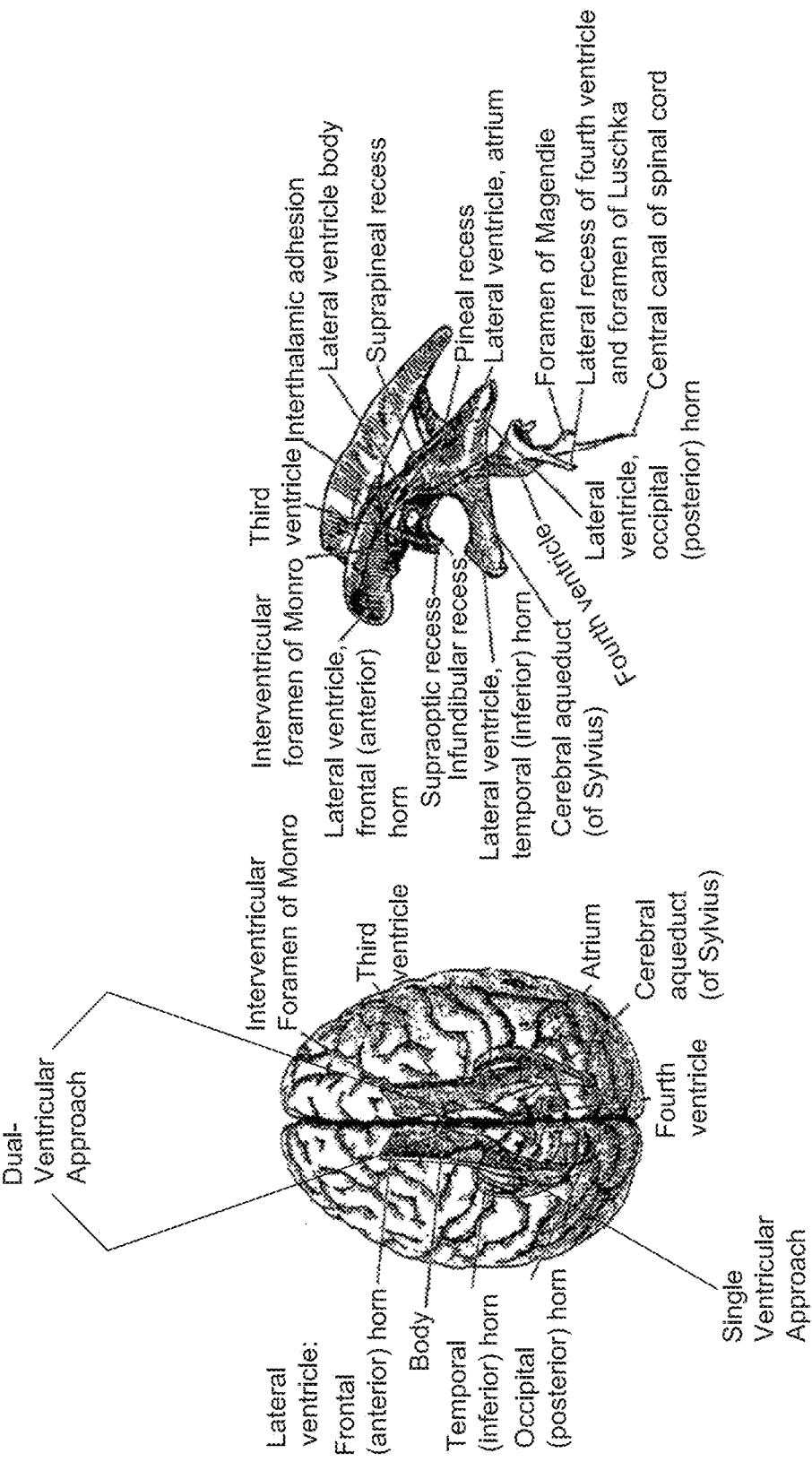
FIG. 6B illustrates one embodiment of the dual- and single-ventricular approaches of the invention.
Figure 6C:
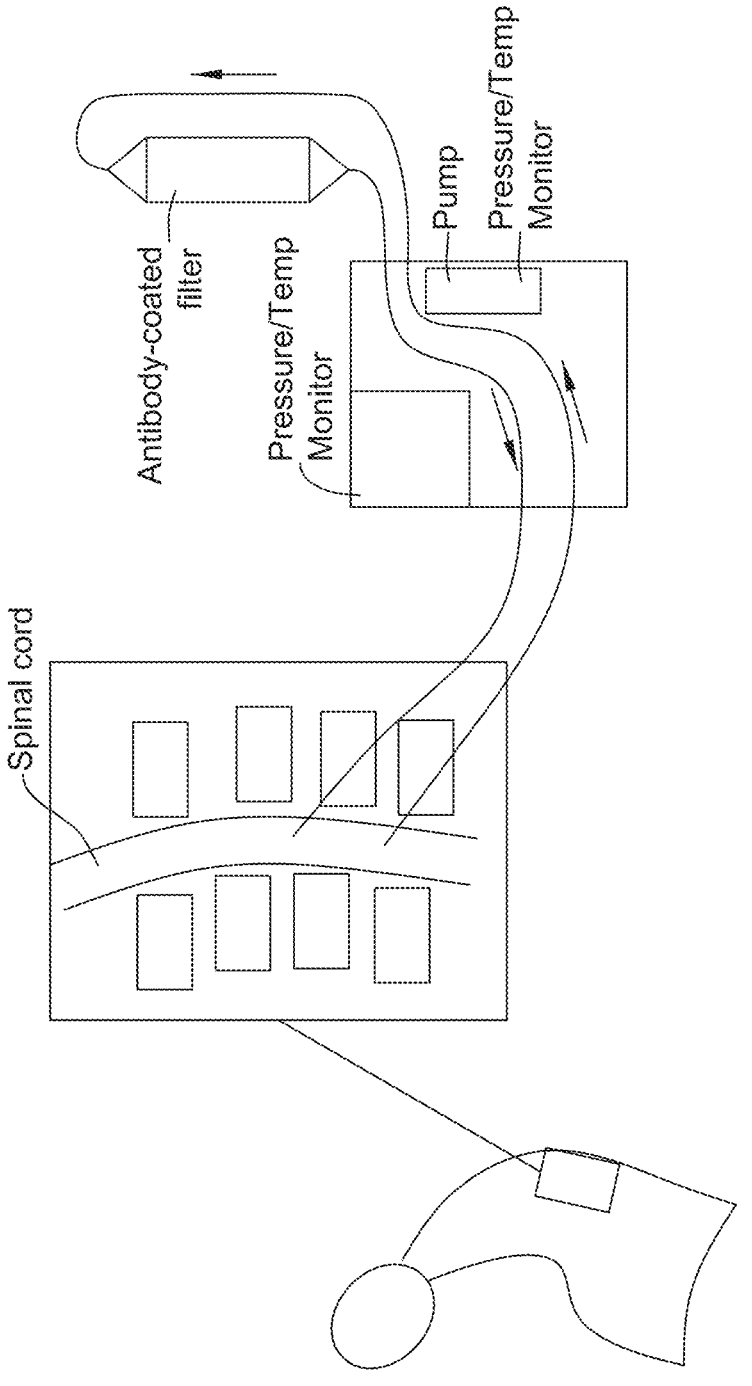
FIG. 6C illustrates one embodiment of the spinal approach of the invention.

Many neurodegenerative disorders are characterized by aggregates of protein fibrils and neurotoxic oligomeric species and infiltrations of pathological inflammatory cell types (e.g., B-cells, T-cells, macrophages) that are implicated in progressive brain degeneration. See, Caughey, B. and P. T. Lansbury (2003). Annu Rev Neurosci 26: 267-98; and Taylor, J. P., J. Hardy, et al. (2002). Science 296(5575): 1991-5. See, Table 1 and FIG. 5. Despite differences in the molecular composition of these protein fibrils as well as the brain regions and cell types affected in each disorder, these diseases share a similar pathological mechanism and therefore, they share similar mechanisms of treatment from a medical device point of view.

TABLE 1

| Disorder | Current US Prevalence (persons) | Proteinacious Deposit | Abnormal Protein | Current Medical Treatment | Current US Cost/Year (billions) |
|---|---|---|---|---|---|
| Alzheimer's Disease (AD) | ~4 million ~22 million by 2025 | Senile plaques and neurofibrillary tangles | Aβ oligomers Tau oligomers | acetylcholinesterase inhibitors | $100 |
| Parkinson's Disease (PD) | ~1 million | Lewy bodies | a- synuclein oligomers | L-dopamine | $ 25 |
| Multiple Sclerosis (MS) | ~350,000 | Demyelinating Plaques | Anti- myelin antibodies | interferon-β | $ 10 |
| Huntington's Disease (HD) | ~30,000 | Intraneuronal Inclusions | Huntingtin oligomers | none | $ 2.5 |
| Amyotrophic Lateral Sclerosis (ALS) | ~30,000 | Intraneuronal inclusions | Insoluble SOD1 | glutamate release inhibitors | $ 1 | the epithelium of the choroid plexus represents an additional barrier between blood and CSF, known as the blood-CSF barrier. Thus, many substances that can leave the capillaries of the choroid plexus cannot enter the CSF. Neurons depend on the precise control of ions and compounds in their extracellular environment for their normal functioning. See, Blumenfeld, H. (2002). "Neuroanatomy through Clinical Cases." 951.

Neurologic Diseases: Diseases affecting the nervous system are among the most devastating and debilitating medical conditions. Increasingly we understand the pathophysiology of a variety of endogenous and exogenous pathogens that can be found within the CSF that produce a direct or indirect deleterious effect on the CNS. This represents an opportunity for intervention and prevention or amelioration of the disease process. Furthermore, the system can be tailored to the individual disease process in a logical, targeted and focused manner.

The concept that numerous distinct disorders of the brain and spinal cord would require a different, disease-specific therapeutic intervention has been challenged by the discov- Immunotherapy: Recently, the immunological concept in the treatment of conformational diseases has gained more attention and immunization approaches are being pursued in order to stimulate clearance, for example in Alzheimer's Disease (AD), of brain beta-amyloid protein (AP) plaques. They include both active and passive immunization techniques. Active immunization approaches employ various routes of administration, types of adjuvants, the use of modified AP epitopes and/or immunogenic AP conjugates. See, Morgan, D., D. M. Diamond, et al. (2000). Nature 408(6815): 982-5. Passive immunization approaches include monoclonal antibodies or specific antibody fractions (Fabs) directed against specific AP epitopes. See, Monsonego, A. and H. L. Weiner (2003). Science 302(5646): 834-8. Plaque clearance as a result of immunotherapy may depend on multiple mechanisms. One theory involves direct interaction of antibodies, or Fab fragments, with the deposits resulting in disaggregation and microglial cell-mediated clearance. A second theory involves antibodies acting as a sink for AP peptide, removing it from the CNS and preventing plaque deposition in the brain by passive redistribution of soluble Aβ oligomers between brain, CSF, and plasma down a concentration gradient. See, Roberson, E. D. and L. Mucke (2006). Science 314(5800): 781-4. Significant data from animal studies exists to support both mechanisms with a substantially reduced A burden in the transgenic mouse model along with improvement in memory disturbances. See, Janus, C., J. Pearson, et al. (2000). Nature 408(6815): 979-82. Promising evidence from A immunization in transgenic mice showing clearance of A plaques and improvement in cognitive disturbances, led to human clinical trials. Unfortunately, human patients actively immunized with an A immunogen developed signs of meningoencephalitis as a consequence of active immunotherapy. See, Orgogozo, J. M., S. Gilman, et al. (2003). Neurology 61(1): 46-54; Bayer, A. J., R. Bullock, et al. (2005). Neurology 64(1): 94-101; and Gilman, S., M. Koller, et al. (2005). Neurology 64(9): 1553-62. Human patients passively immunized with antibodies against the A protein developed neutralizing endogenous antibodies against the anti-A antibodies, nullifying the therapeutic effect of the passive immunotherapy, and also potentially resulting in a detrimental increase in A protein. See, Hock, C., U. Konietzko, et al. (2003). Neuron 38(4): 547-54; Nicoll, J. A., E. Barton, et al. (2006). J Neuropathol Exp Neurol 65(11): 1040-8; and Melnikova, I. (2007). Nat Rev Drug Discov 6(5): 341-2.

The primary concerns with both active and passive immunization lie in the pro-inflammatory consequences following immunization, which may lead to overactivation of microglia. In addition to the multiple inflammatory pathways thought to be involved in AD there are particular inflammatory pathways that are activated specifically following microglial stimulation, including release of proteases and cytokines, and activation of the oxidative burst that may exacerbate brain inflammation and AD-related neurodegeneration in the process of scavenging A. In addition to inflammation, concerns exist for development of auto-antibodies with immune tolerance and the inability to reverse the treatment once administered. Furthermore, for redistribution of soluble A oligomers down the brain, CSF plasma concentration gradient, it is unknown whether A is degraded in the plasma or taken up by specific organs. To address these concerns, one needs a therapy that prevents antibody from entering the CNS while still sequestering the toxic protein of interest.

The CSF Purification system described in the present invention serves as a broad platform technology for the treatment of a number of diseases affecting the nervous system. Several examples along with detailed rationale are provided below for a number of neurologic diseases to which there are presently limited or ineffective therapies.

It would be desirable to provide improved and alternative methods, systems, kits for the processing, purification and/or modification of CSF for a variety of purposes. The current invention possesses numerous benefits and advantages over previously described methods. First, the removal of agents based on size (such as red blood cells and their breakdown products in cerebral vasospasm, T- and B-cells in MS, auto-antibodies in GBS). With the recent advances in nanotechnology and ultrafiltration, it is now possible to remove agents on the nanometer scale as opposed to micrometer, nearly a 1000.times. improvement in targeted filtration than previous systems. Prior filtration methods based on size were limited to 0.2 micron filters allowing the majority of smaller toxic molecules to pass directly through the filter and back to the patient.

Second, with the recent advances in immunotherapy, the current invention applies ex-vivo immunotherapy targeted at removal of pathogenic molecules from the CSF that directly affect the CNS. Antibodies provide an unprecedented level of specificity to molecules that are too small to remove by present-day size filters. In vivo immunotherapy applications have been met with a number of serious complications including encephalitis and death as described above. By securing the antibody to an immunoaffinity column, for example using a streptavidin-biotin system (strongest chemical bond known), CSF is processed over the antibody cartridge and sequestration of toxic oligomers and/or proteins can be achieved with no risk of systemic antibody delivery, encephalitis or death. The use of biologic separation (including Abeta and Tau proteins in AD, alpha-synuclein in PD, etc.) can be beneficially applied to a number of diseases by altering the neuro-immune axis using a platform ex-vivo immunotherapy approach.

Third, modulation of temperature by mild, moderate or severe hypothermia has been shown to have beneficial effects in terms of neuroprotection. Localized cooling of the CNS without systemic effects on the heart, liver or kidney may provide an added advantage in a number of diseases including stroke, traumatic brain injury and spinal cord injury. Such objectives are met by the invention described hereinafter.

1. Systems of the Invention

The CSF purification system includes a multi-lumen catheter incorporating two or more lumens for the efficient exchange of CSF from either cranial and/or spinal CSF spaces. The present system creates a dynamic circulation with significant mixing within the cranial or spinal CSF space. The present invention allows for the processing of large volumes of CSF in a short amount of time while minimally impacting the endogenous intracranial/intraspinal pressure and volume.

The purification (or compound removal) schema can be tailored to a specific disease or group of diseases based on a number of features, including size, affinity, biochemical properties and/or temperature, but more specifically purification schema based on diffusion, size-exclusion, ex-vivo immunotherapy using immobilized antibodies or antibody fragments, hydrophobic/hydrophilic, anionic/cationic, high/low binding affinity, chelators, anti-bacterial, anti-viral, anti-DNA/RNA/amino acid, enzymatic, magnetic or nanoparticle-based systems. The system allows for passive flow but also includes a mechanism of active pumping with transient or continuous flow such that inflow and outflow are relatively equal to one another. Furthermore, a number of safety measures (including, but not limited to, pressure sensor, velocity detector, bubble detector, pH, temperature, osmotic equilibrium, blood pressure, transmembrane pressure sensor) to ensure patient safety are included. Pressure sensors to continuously record/maintain/adjust intracranial and/or intraspinal pressures are also available. Programmable control of intake, output and overflow exhaust valves are additional contemplated features. The system is adjustable to a broad range of biologic parameters and flows. Alarms and automatic on/off settings are further included to provide a signal for immediate attention and interrogation of the system. A given volume of CSF is outside the patient at any one time, less than that which produces symptoms associated with spinal headache or overdrainage.

Figure 7:
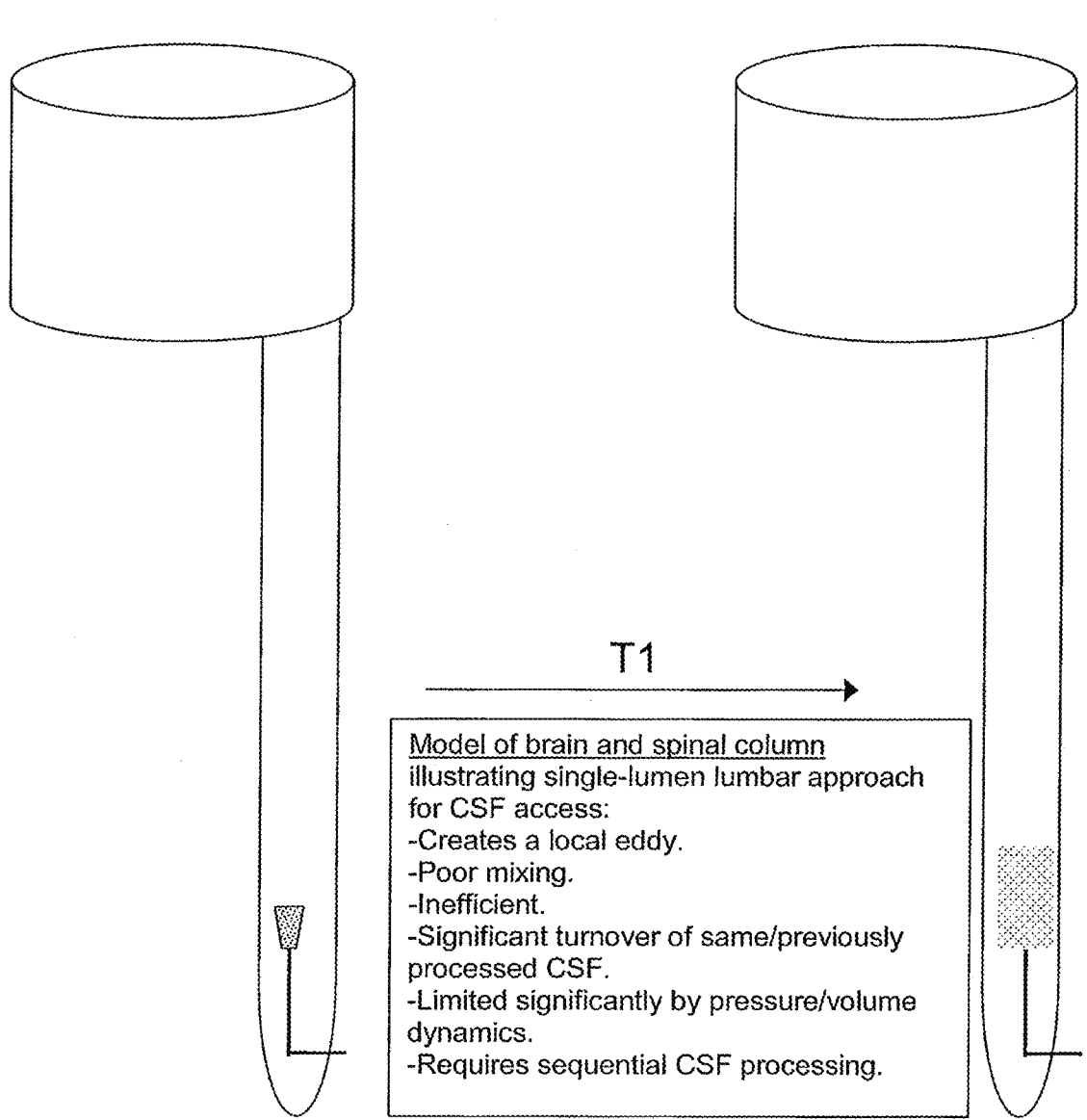
FIG. 7 illustrates a schematic of a single lumen system. A single-lumen system creates a local eddy (shading) with minimal mixing or access to cranial CSF.

Accordingly, the CSF purification/conditioning systems provide a dual/multi-lumen catheter design. Flow studies have indicated that a dual or multilumen catheter with inflow and outflow separated from one another by an appropriate distance serves to create and maintain a dynamic circulation and efficient mixing/exchange of CSF. Given the normally occurring variations in patient anatomy, such a distance may vary by individual. Therefore a system which allows for the variation in this distance in situ or prior to application (i.e., implant) would provide a further improvement in performance for such systems in there application across the population. The flow dynamics created with such a system are dramatically different than a single lumen system or a system where the inflow and outflow points are closely spatially located (FIG. 7). Dye studies clearly demonstrate that the present system incorporating catheters with dual or multilumen designs and spaced apart inputs and outputs allow for a greater turnover of unprocessed CSF per minute, or more efficiency with minimum mixing of unprocessed and processed CSF, thereby accessing a significantly larger portion of the entire CSF volume in a shorter period of time (FIG. 8A). The present system design has dramatic effects on CSF physiology and flow. In the present dual lumen system, the distance of separation of inflow and outflow sites determines the maximum "column of CSF" that can be processed and cleared initially (FIG. 8B). The catheter system with two or more lumens as well as multiple holes for inflow and outflow along the length of the catheter not only minimizes clogging but provides greatly increased turnover and access to the basal cistern, ventricular, cranial as well as spinal subarachnoid CSF than previously described anywhere in the literature. The greater efficiency at removing compounds of interest arises from less reprocessing of the same fluid (FIG. 8C).

Figure 12A:
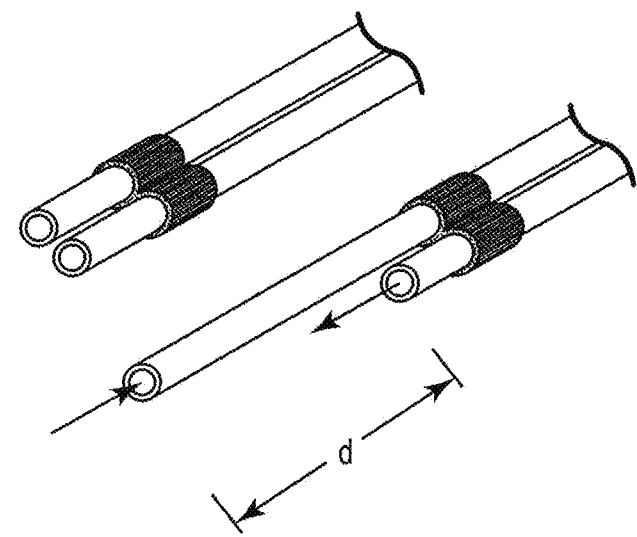
FIG. 12A illustrates two catheters bound by a double collar. The collar is fixed to one catheter and slips on other such that the distance "d" between the two ends is adjustable. In this case, the inflow catheter is interfaced with the slipping portion of the collar.
Figure 12B:
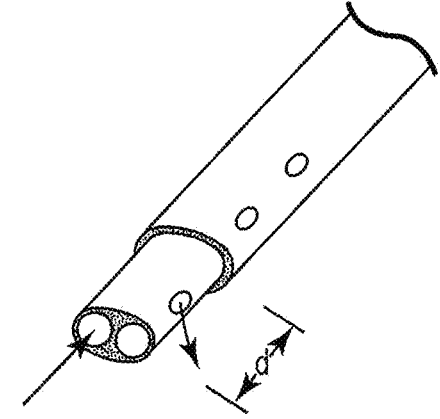
FIG. 12B illustrates a dual lumen catheter that is encircled by a tight fitting thin walled cannula. The outflow lumen of the inner catheter has side ports such that, as the cannula is pulled back additional side ports or openings are exposed, thereby increasing the distance between the inflow and outflow.
Figure 13A:
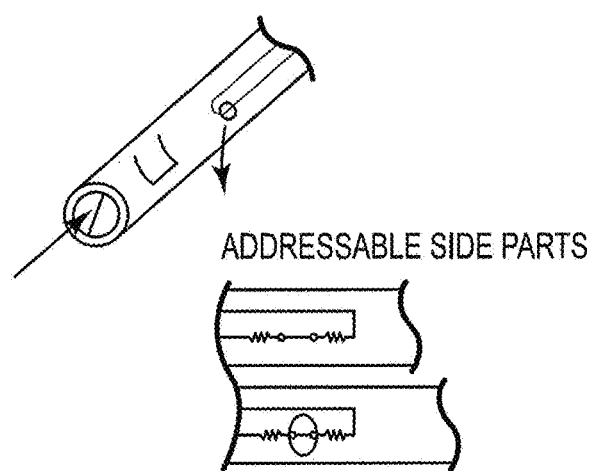
FIG. 13A illustrates a dual lumen catheter with addressable holes on one lumen.
Figure 13B:
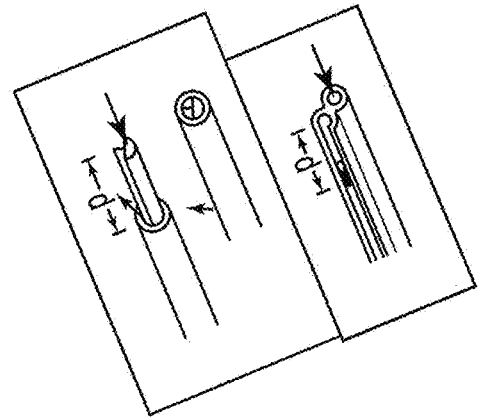
FIG. 13B illustrates a two catheter system creating a dual lumen catheter. As shown, the outflow catheter is created by the space between the inner and outer catheters.
Figure 14A:
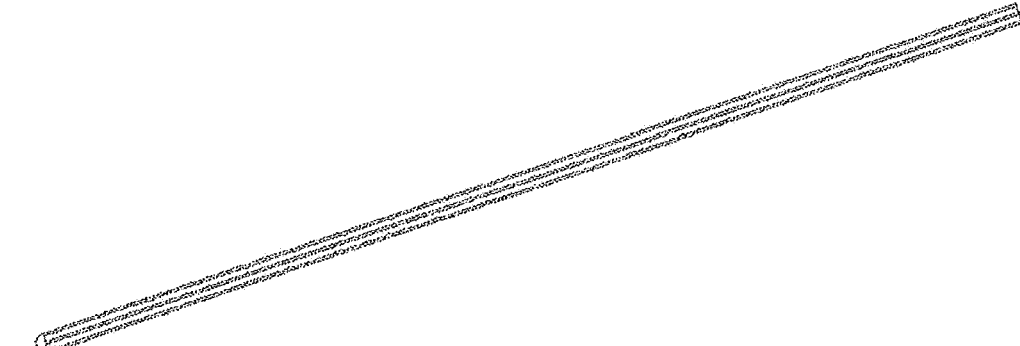
FIG. 14A illustrates a dual lumen catheter with partially overlapping side ports for use in sub arachnid to ventricular access. The holes surrounded by parenchyma would be sealed by the parenchyma. These would include the overlapping portion.
Figure 14B:
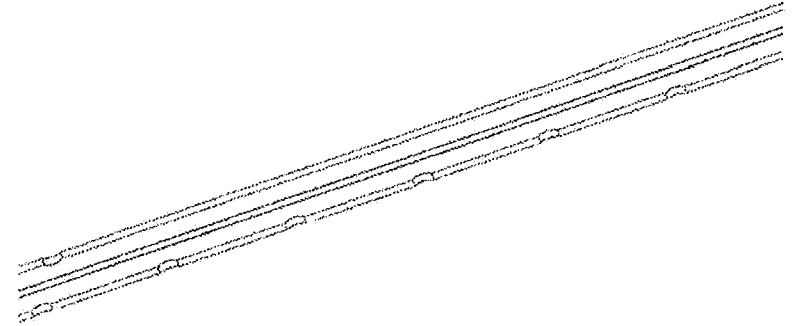
FIG. 14B illustrates a close-up of an end showing one overlapping hole on the left.
Figure 14C:
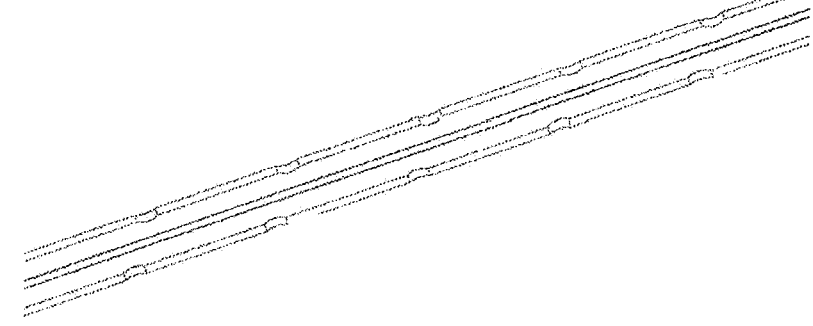
FIG. 14C illustrates a middle section showing overlapping holes.
Figure 15A:
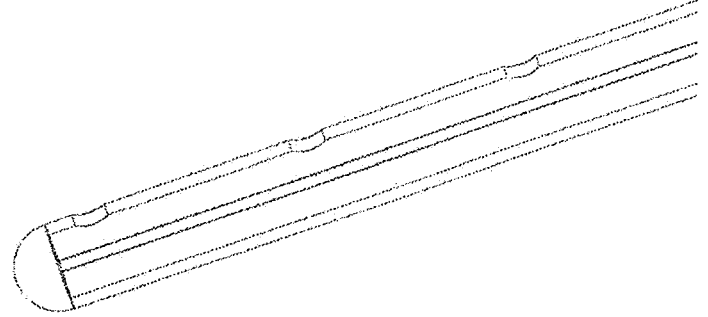
FIG. 15A illustrates an end section.
Figure 15B:
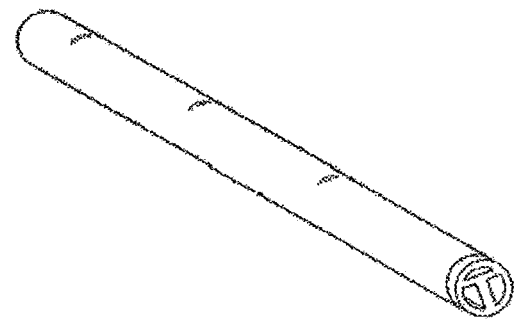
FIG. 15B illustrates a catheter incorporating multiple balloons. The inflow and outflow lumens are seen on either side of the base "T-section." The balloon inflation lumen is above the T-section. The three balloon inflation ports can be seen from the top through thin membranes which form the balloons.
Figure 15C:
FIG. 15C illustrates a cross-section of an end with inflow and balloon inflation lumens visible along with an inflation port.
Figure 16A:
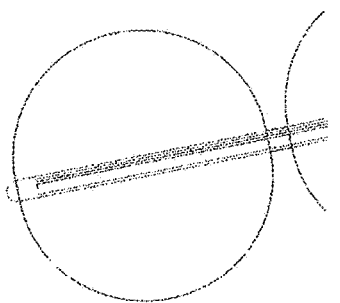
FIGS. 16A-C illustrate balloons inflated. A catheter can contain single or multiple balloons. The balloons can be spherical or long. Long slender balloons are well-suited for a spinal column space. The distance between balloons can be uniform or of different lengths.
Figure 16B:
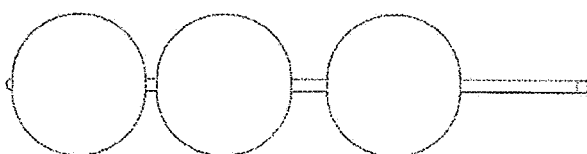
Figure 16C:
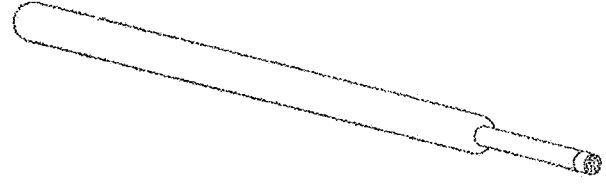

Simple single lumen catheter systems produce only a local eddy, with minimal mixing and therefore recirculation of much of the same, previously processed CSF. Such single lumen systems do not generate enough mixing to adequately draw or circulate fluid from the cranial CSF space that bathes the brain. In vitro studies indicate that the rate of mixing, the amount of new CSF turned over per minute as well as the access provided to turning over the cranial and spinal CSF volume multiple times using the present invention results in a much more rapid, efficient and feasible CSF processing system that provides access to the entire CSF system than that attainable using a single lumen system. The present invention provides the ability to run parallel removal and return flows as opposed to sequential. Furthermore, the multilumen catheter can also incorporate an adjustable distance between the inflow and outflow areas, providing additional freedom for creating mixing and circulation of CSF (FIGS. 12A-12B).

Figure 9B:
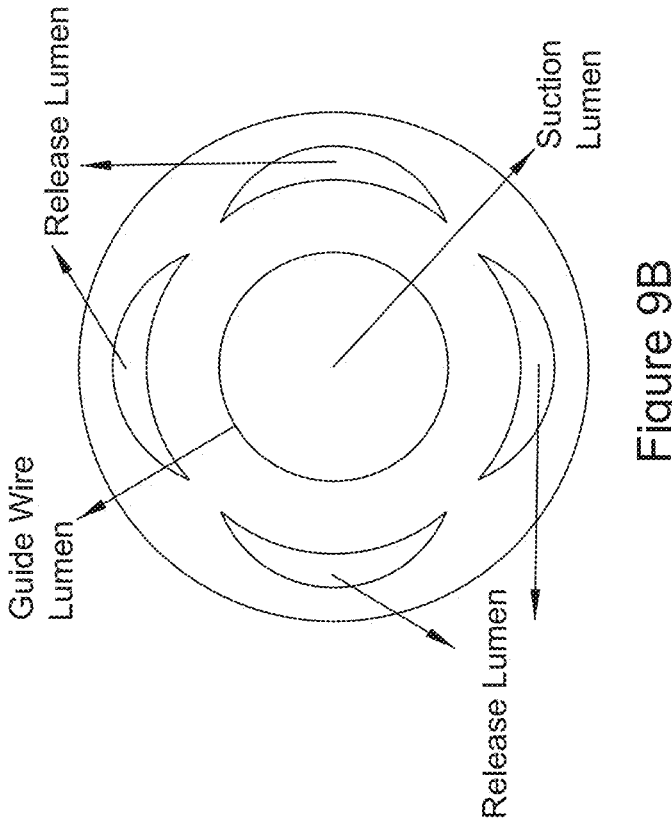
FIGS. 9A and 9B illustrates cross-sections of sample dual or multilumen catheters, respectively, for use in the CSF space. These are but two examples of many embodiments that may be envisioned to achieve one of the ultimate goals of the invention which is a method to provide efficient mixing and turnover of CSF.
Figure 9A:
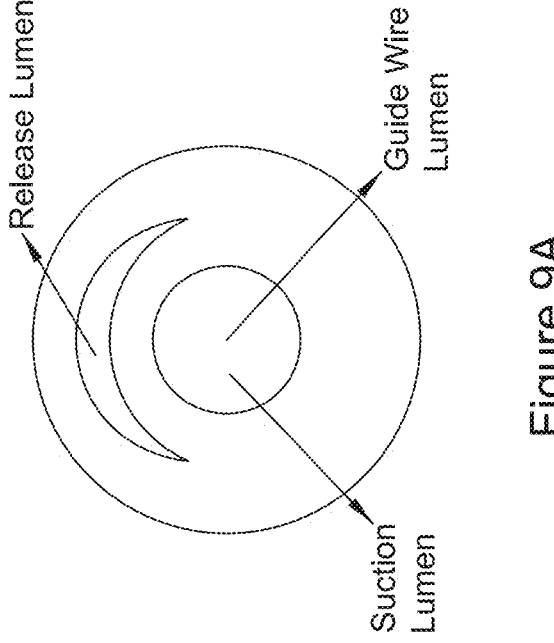

Parallel or continuous processing of removal and return flows using the multilumen systems of the invention provides several advantages over single lumen systems that require sequential processing. First, parallel processing is more efficient and requires fewer steps than sequential processing. Multilumen systems that provide for continuous, parallel processing also can be conveniently automated and are more suitable for implantation. Because continuous, parallel processing systems can be designed to be closed, there is less need for human or manual intervention and better control of sterility. Moreover, continuous flow processing is not limited by the volume limitation on the amount processed; a wide range of flow rates and volume exchange can be accomplished (FIGS. 9A-9B). The only limitation is the dead space volume of the tubing, particularly in partially external systems.

The shape of the lumens is also a factor to consider. Studies have shown that simple circular lumens are more prone to clogging and necessitating repeated irrigation and/ or catheter replacement. The dual/multi-lumen catheter systems described herein include a plurality of designs including, but not limited to, a combination of variable size and orientations of circular, oval, square, etc. designs to avoid catheter clogging. A combination of transient and/or continuous flow facilitates the maintenance of lumen patency and significantly decreases the risk of clogging associated with present day systems. The dual or multilumen system also allows for reversal of flow and rapid unclogging by intermittent reversal of flow by the pumping system. A dual lumen system provides the further advantage of allowing increased time periods in a particular flow direction by moving the clogging agents further away from the input.

Figure 10A:
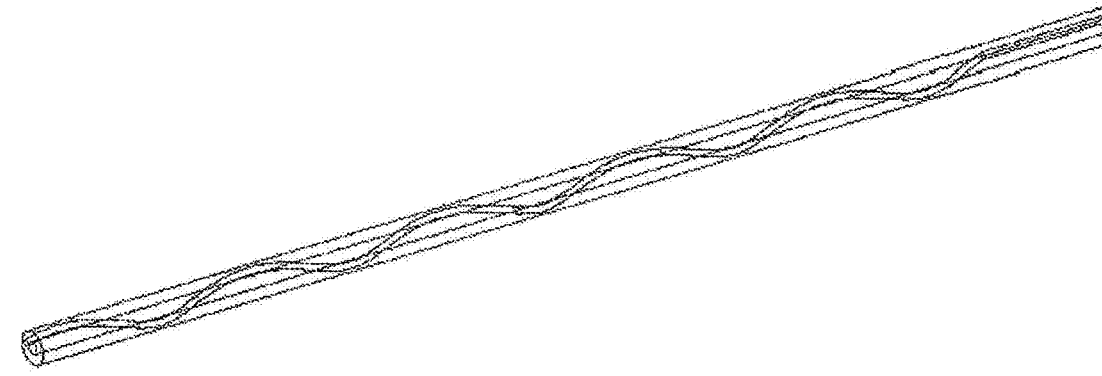
FIGS. 10A and 10B illustrate catheters with helical out flow paths which induce additional mixing at various outflow points.
Figure 10B:
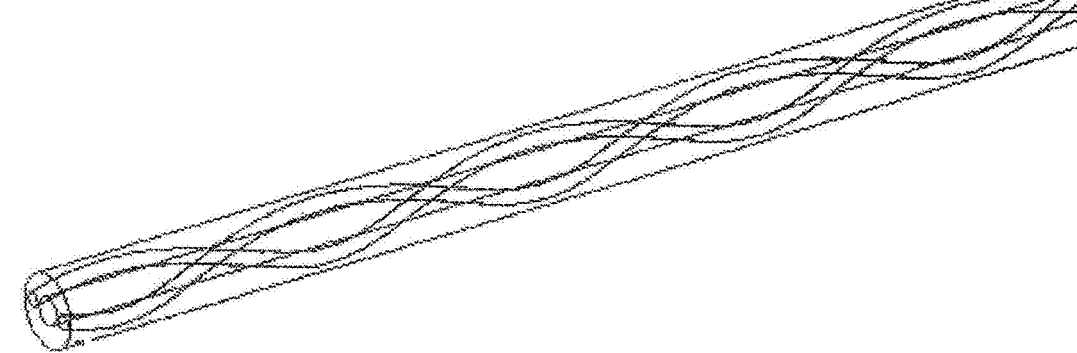
Figure 11A:
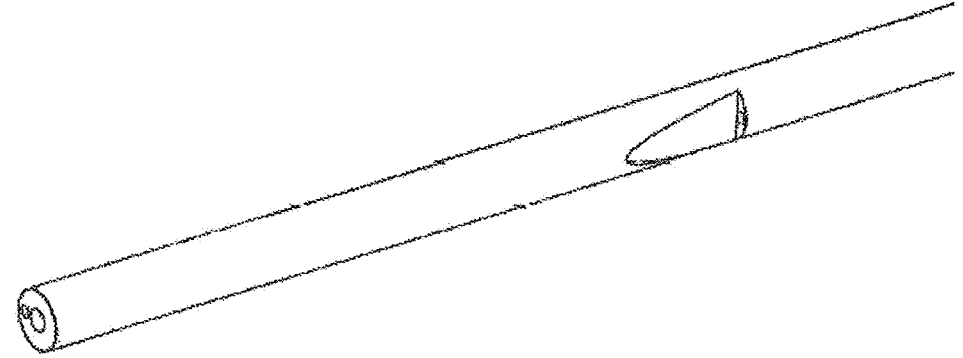
FIG. 11A illustrates dual helical outflow paths exiting at different points along the catheter. The catheter comprises a single central inflow path. As described herein, the paths can be reversed, for example, by a pump mechanism. Therefore, a catheter with a single inflow path and multiple outflow paths could become a single outflow path with multiple inflow paths.
Figure 11B:
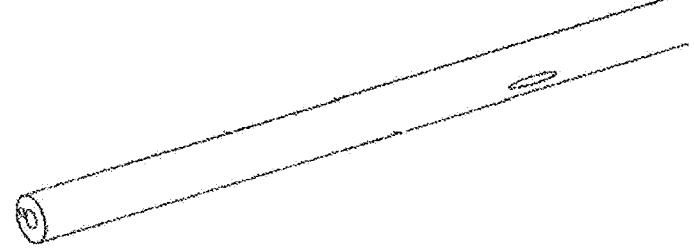
FIG. 11B illustrates how helical path directional changes as another means of creating a directed flow.

The distal portion of the catheter can be constructed to promote maximal mixing and exchange of returned and unconditioned CSF upon return of the conditioned CSF. The elements that enhance mixing can be external or internal to a patient's body. One example is a helical or double helical design (i.e., FIGS. 10A-10B), with or without bellows, to create maximum disruption/turbulence of passive CSF flow and more complete mixing and exchange of endogenous for processed CSF. Other examples include using jetting or directing outflow such that eddies or turbulence are created and thereby enhance mixing (FIGS. 11A-11B).

The catheter can contain a number of distal geometries to enhance mixing and exchange of CSF. One example is a T-catheter lumbar design (i.e., FIGS. 13 and 15) in which both entry and exit lumens are inserted as a single catheter and the distal lumen either folds away or is deployed using a release mechanism such that one maximizes the distance between inflow and outflow sites and makes maximal surface area contact with the CSF space. Another example is the addition of small fins, a nonplanar surface, ribbed portions or a small balloon system (i.e., FIGS. 15 and 16) anywhere along the length of a cranial or spinal catheter that creates further mixing and exchange of endogenous and processed CSF. Examples of catheter designs that promote flow turbulence and mixing are shown in FIGS. 10A-16.

A portion of the purification system can be incorporated into the catheter itself by fashioning it with a membrane that allows for the passive filtration of the endogenous CSF and/or equilibration with the processed CSF.

In some embodiments, the catheter includes radio-opaque markers for the accurate localization and confirmation of catheter tip location in the cranial or spinal CSF spaces. The radio-opaque markers can then be visualized using simple X-ray or computerized tomography. A variety of other methods can be utilized to confirm accurate catheter deployment and placement. This includes the use of an endoscope to directly visualize placement of the cranial or spinal catheter. This method may especially be useful in those patients with small cranial ventricles containing CSF or in those patients with spinal stenosis or scoliosis, where lumbar access is challenging.

One of the major concerns of any implanted device is the risk for infection. The risk of infection in the CSF is serious and includes meningitis, encephalitis and even death. A number of safety measures can be incorporated into the present invention to minimize and/or eliminate the possible risk of patient infection. First, the proximal end of the catheter can be tunneled a variable distance away from the entry site to minimize the risk of organisms tracking back in from the skin surface entry site. Second, meticulous care on a daily basis to clean the site of catheter access can be performed by a nurse or taught to the patient. Third, immediately before catheter placement as well as during the time the catheter remains indwelling during CSF processing and immediately after removal, antibiotics can be administered to the patient to further reduce the risk of infection. Fourth, the catheter system itself can be impregnated with a specific antibiotic of choice. Fifth, a specific metal that can produce a transiently charged surface, which has been shown to deter bacterial ingrowth and the incidence of catheter infections in general, can be incorporated. Sixth, an antibiotic of choice can be delivered into the CSF a certain time before, during or after CSF processing to further eliminate the risk of bacterial seeding or infection. Finally, an antibiotic cuff at one or more places along the catheter system can be placed to further reduce any risk of infection.

Another concern of any catheter system is the risk of kinking or physical obstruction. The current invention incorporates a number of safety sensors to ensure that inflow and outflow are generally relatively equal. However, in addition, incorporating certain shape memory alloys in catheters (for example, in one of the lumens of FIG. 9B) for use in the CSF space can be an added strategy of preventing kinking, maintaining shape, and allowing for maximum access of the CSF space. Nickel titanium is a shape memory alloy also commonly referred to as Nitinol. Above its transformation temperature, it is superelastic and able to withstand a large amount of deformation. Below its transformation temperature, it displays a shape memory effect. When it is deformed, it will remain in that shape until heated above its transformation temperature, at which time it will return to its original shape. Nitinol is typically composed of about 55% nickel by weight and making small changes in the composition can change the transition temperature of the alloy significantly which makes it suitable for many applications in medicine. In some embodiments, the catheter incorporates nickel titanium in its manufacturing. Such a catheter would allow for the easy entry of the catheter via the cranial or spinal access routes due to superelastic nature of Nitinol, while once in the CSF space the catheter would be return to its prior structure due to its shape memory. Nitinol's physical function resembles biological muscle; when activated it contracts. The contraction movement may be applied to any task requiring physical movement with low to moderate cycling speeds. The small size, light weight, ease of use and silent operation allow it to even replace small motors or solenoids. Such a catheter system that is internally adjustable and tailored to access varying areas of the cranial or spinal CSF space while minimizing the risk of kinking and catheter obstruction would be an additional feature in the present invention.

In some embodiments, the systems incorporate a conductive material or heat-exchange element into a portion of the catheter system (for example, in one of the lumens of FIG. 9B) that would allow for the rapid and direct alteration of the CSF space for those disorders needing rapid adjustment of temperature. The neuroprotective effect of profound hypothermia has long been recognized, but use of hypothermia for the therapy of neuronal injuries was largely abandoned because of management problems and severe side effects, such as cardiac arrhythmia, shivering, infections, and coagulation disorders. In the past decade, it has come to be recognized that mild (34° C. to 36° C.), moderate (34° C. to 28° C.) and severe (<28° C.) hypothermia allow for therapeutic modulation of temperature and may substantially avert brain damage caused by ischemia in both experimental stroke and other neuronal injuries. After focal cerebral ischemia, hypothermia reduced infarct volumes up to 90% and has been found to have significant beneficial effects on patients suffering from traumatic brain injury or spinal cord injury. By contrast, hyperthermia has been shown to have a significantly negative effect on CNS histopathology and outcome.

Such a temperature adjustable cooling catheter designed specifically for the cranial or spinal CSF space, which can be used independently or in conjunction with an extracorporeal refrigerant system described in the prior literature, provides an added mechanism of rapid and direct CNS cooling without the systemic side effects seen on the heart or coagulation cascade seen when cooling the entire blood volume. Such a CSF cooling system has multiple utilities, including but not limited to, stroke, traumatic brain injury (TBI), spinal cord injury (SCI) and can be used separately or in conjunction with various purification/conditioning schema discussed above and herein. Temperature sensors of endogenous as well as processed CSF in addition to systemic body temperature can be incorporated into the heating/cooling system to appropriately record/maintain/adjust temperature.

The present systems allow for a number of different CSF inflow and outflow connections for the processing of CSF between any point in the CSF system such that total inflow and outflow are relatively equal. The spatial location of the inflow and outflow ports are sufficiently distant to allow for CSF flow throughout a major portion or the entire CSF space. The custom cranial or spinal catheters can be introduced via a number of routes, including but not limited to: single ventricular insertion, dual ventricular insertion, single level spinal insertion, dual/multi-level spinal insertion and ventriculo-spinal. In some embodiments, a first catheter is inserted into a brain ventricle or into the cervical spine, and a second catheter is inserted into the lumbar spine. In addition, any of the above systems could be fashioned to exchange CSF from any two points within the subarachnoid space. One example is a ventricular catheter with entry/exit sites communicating with the subarachnoid space overlying the adjacent brain parenchyma.

The present systems allow for the active movement of a large volume of CSF over time, and do not require the removal or diversion of CSF from the human body. Due to the varying entry and exit sites in the custom catheter, the system allows for the production of active, in addition to the normally passive, CSF flow. The active movement of CSF can be generated in a number of ways including but not limited to motorized pumps for active CSF withdrawal and return. Furthermore, the pump system can have a variety of mechanisms which facilitate the requirement that inflow and outflow are relatively equal. Examples of suitable pumps include rotatory, syringe-driven, volumetric, peristaltic, piston, pneumatic, bellows, electromagnetic, magnetostrictive, hydraulic, and the like. The pumps can be a single apparatus with bi-directional functionality or two unidirectional pumps that are in communication with one another. There are several pumping mechanisms available to reach the desired endpoint of creating active, in addition to the normally passive, flow of CSF. The pump can be external or internal to the patient's body. Internal or implantable pumps are known in the art (e.g., an Archimedes screw pump).

In some embodiments, the systems provide a customizable conditioning system based on the specific disease process being addressed. Removal of specific compounds can be targeted based on size-exclusion, specific antibodies, hydrophobic-hydrophilic interactions, anionic-cationic exchangers, compounds with high-low binding affinity, antibacterial, anti-viral, anti-DNA/RNA, immunotherapy-based, immuno-modulatory, enzymatic digestion, etc. In addition to the variety of neurochemical filtration approaches, other filtration systems based on electrome-chanical basis including radiofrequency, electromagnetic, acoustic wave, piezoelectric, electrostatic, atomic force and ultrasonic filtration can be employed. Other features can be added to the filter system including a differential centrifugal force to aid in the rapid separation of items of interest, e.g. ultrafiltrate, proteins, cells, etc.

In some embodiments, a cartridge-based schema can be employed for rapid changing or combinations of the afore-mentioned purification-based schema. For example, a sys-tem combining size, antibody and charge based approaches is envisioned with a single or multiple cartridges for the purification, such that when the time came for replacement of the purification filter, antibody, etc., it could be done in an easy to use, rapid exchange system. The conditioning system or chromatographic cartridges (e.g., biospecific interaction, ionic exchangers, size exclusion) can be external or internal to a patient's body. In some embodiments, the conditioning cartridges or filters are contained within one or more lumens of the multilumen catheters. In some embodiments, the lumen of the catheters, or sections thereof, are coated (e.g., by covalent or non-covalent binding) with chromatographic moieties (e.g., biospecific capture moieties, including anti-bodies and nucleic acids, cationic or anionic exchangers, hydrophobic moieties, and the like).

In some embodiments, the systems include sensors for the intermittent or continuous monitoring and/or sampling of CSF levels of specific compounds or parameters of interest. For instance, in cerebral vasospasm, one could serially sample and quantify levels of red blood cells, hemogolobin, endothelin, or other molecules and have an indication of how much the system has cleared the CSF. Similarly in Alzheimer's, one could measure levels of A, Tau or other molecules and have an indication of production or removal of specific items of interest. Sensors may be utilized to record/maintain/adjust levels of specific compounds in the CSF noninvasively.

1. Methods of Use a. Methods for Conditioning Cerebrospinal Fluid

The invention provides for methods for conditioning cerebrospinal fluid in a patient using the systems of the invention. The cranial or spinal catheters are placed using appropriate anatomic landmarks which are known to those skilled in the art such that said custom catheter is in contact with the CSF space of interest. The cranial catheter is placed at specific points and trajectory such that one enters the ventricular CSF space or cranial subarachnoid space over-lying the brain parenchyma. In the case of a spinal catheter, a cannula is placed at any point along the spinal canal (often lumbar) and provides a conduit for which to place said custom spinal catheter into the CSF space. In particular, a multi-lumen spinal catheter can be inserted between a patient's lumbar vertebrae, for example, using a needle cannula to advance the catheter. In some embodiments, a sacral catheter is inserted in the sacral region above S1. In some embodiments, a lumbar catheter is inserted in the lumbar region above L5, L4, L3, L2 or L1. In other embodiments, a spinal catheter is inserted between thoracic or cervical vertebrae. For both spinal or cranial entry, the patient can be supine, sitting, or at any angle between 0° and 90°.

CSF is removed from the cranial or spinal CSF space passed through a disease-specific conditioning system and returned to a different location in the cranial or spinal CSF space. CSF is removed using a combination of natural passive flow but augmenting it with a pumping mechanism to produce an active CSF flow dynamics. The volume of CSF outside the body at any given time is less than that which would produce a spinal headache or symptoms of overdrainage (about 40 ml). The locations of the catheter may vary but include single, multi-lumen or a combination of catheters placed via single ventricular insertion, dual ventricular insertion, single level spinal insertion, dual/multi-level spinal insertion and ventriculo-spinal.

One exemplification includes use of a single level spinal insertion that is inserted in the lumbar space and fed crani-ally such that the catheter tip is in the cervical region. In this example, CSF inflow may be from the cervical portion and output from the lumbar portion and/or anywhere along the length of the multi-lumen catheter, depending on the number and location of exit ports along the outflow lumen. In another embodiment, inflow can be at the lumbar region and outflow at the cervical, subarachnoid or ventricular regions. In another embodiment, both the inflow and outflow ports are in the ventricular space, for example, with one port in a first ventricle and a second port in a second ventricle. In another embodiment, the inflow and outflow ports are located at different sides of the same ventricle.

The flow rates may be varied and are limited by the pressure differential placed on the catheter walls, but gen-erally can be in the range of 0.04 ml/min to 30 ml/min, for example, about 5 to 20 ml/min, for example, about 0.5, 1, 2, 5, 8, 10, 12, 15, 20 ml/min.

The CSF is then conditioned using a variety of mecha-nisms as described above and generally include size, bio-specific and/or temperature-mediated mechanisms. In per-forming the conditioning step, the removed or withdrawn CSF is contacted with one or more substrates comprising chromatographic, electrochemical or electromechanical selection agents.

The methods provide a customizable conditioning schema based on the specific disease process being addressed and the target compounds to be removed from the CSF. Depend-ing on the one or more target compounds to be removed (e.g., proteins, oligomeric peptides, amino acids, nucleic acids, bacteria, etc.), the CSF can be contacted with one or more substrates comprising size-exclusion filtration, hydro-phobic-hydrophilic interactions, anionic-cationic exchang-ers, compounds with high-low binding affinity, anti-bacte-rial, anti-viral, bio specific interactions including nucleic acid hybridization and immunoaffinity (e.g., antibodies or non-antibody binding proteins), enzymatic digestion, or a combination thereof. Antibodies can be whole immuno-globulin molecules or fragments thereof (e.g., FAb, single chain variable regions (scFv), variable regions). Non-anti-body binding molecules, for example, based on A-domain scaffolding, also find use. In addition to the variety of chromatographic approaches, filtration systems based on electromechanical bases also find use, including radiofre-quency, electromagnetic, acoustic wave, piezoelectric, elec-trostatic, atomic force and ultrasonic filtration can be employed. The CSF may also be subject to differential centrifugal force to aid in the rapid separation of items of interest, e.g. ultrafiltrate, proteins, cells, etc.

In some embodiments, the CSF is contacted with multiple substrates, e.g., combining size, bio specific and charge-based selection criteria. The conditioning step can be per-formed external or internal to a patient's body. In some embodiments, the conditioning substrates are contained within one or more lumens of the multilumen catheters. In some embodiments, the lumen of the catheters, or sections thereof, is coated (e.g., by covalent or non-covalent binding)

with chromatographic moieties (e.g., biospecific capture moieties, including antibodies and nucleic acids, cationic or anionic exchangers, hydrophobic moieties, and the like).

The concept of ex-vivo immunotherapy (i.e., immunoaffinity) using the CSF is itself a broadly applicable and novel component of the present invention. A number of conditions affecting the nervous system are now better understood and a common feature is a disruption in the neuroimmune axis or weak points in the blood brain barrier allowing B-cells, T-cells and the humoral and cell-mediated immune responses. In both instances, the normal neuronal architecture is victim to a broad range of neuro-inflammatory components and reactive oxidative stress proteins. The present invention allows for targeted removal of inflammatory cells and proteins and elimination and/or neutralization of oxidative stress proteins.

With regards to immunotherapy, present day active and passive immunotherapy treatments carry significant risk of encephalitis or generalized neuronal inflammation. By harnessing the immunotherapy components in an immobilized immunoaffinity approach, one can bring the CSF to the antibody and prevent any risk of mounting a generalized immune response against oneself. Furthermore, this eliminates the risk of autoantibodies against systemically delivered immunotherapies, which could have devastating effects and high mortality in a subset of patients. Cartridge-based schema would allow for further rapid replacement of the conditioning approach.

The methods contemplate the periodic re-use or re-charging of the filtration/processing component of the system. For instance, in the ex-vivo immunotherapy approach, a specific eluent can be used to release the captured oligomers or proteins and regenerate the active antigen binding sites on the antibodies. Furthermore, this eluted compound represents a purified human protein which can then be used as a "neuropharmaceutical" agent. For example, in Alzheimer's disease, purified A or Tau components may then be released and used for a variety of other commercial or research studies involving the structure-function activity of disease-specific compounds in human disease. Also, the ability to automatically or periodically collect CSF or specific subcomponents and store/freeze creating a CSF bank for specific disease processes is contemplated.

The conditioned endogenous CSF is then returned back to a CSF space in a different location than from which it was drawn. The second location or distal port for outflow or output is at a sufficiently different location from the first location or proximal port for inflow or input to create mixing of the conditioned and unconditioned CSF through a majority of the CSF space. For example at least about 50%, 60%, 70%, 80%, 90% of the conditioned and unconditioned CSF in the CSF space can be mixed. The inflow and outflow ports usually can be at least two vertebrae apart, for example, if both ports are in the spinal area. In other embodiments, one of the inflow or outflow ports can be in the spine (e.g., sacral, lumbar, thoracic or cervical) and the other inflow or outflow port can be in the subarachnoid or ventricular space. In some embodiments, both the inflow and outflow ports are in the ventricular space, for example, where the inflow port is in a first ventricle and the outflow port is in a second ventricle (dual-ventricular embodiment). Depending on the design of the system, the quantitative distance between the inflow and outflow ports can be at least about 4 cm, for example, at least about 5 cm, 8 cm, 10 cm, 12 cm, 15 cm, 20 cm, 30 cm, 40 cm, 50 cm, or 60 cm, or longer, depending on the length of spine of an individual patient.

As discussed above and herein, one or more different geometries in the distal portion of the outflow lumen of the catheter facilitate turbulence mixing upon return of the conditioned CSF. For example, the distal portion of the outflow lumen can be configured to be a single or double helical conformation, contain multiple exit ports (i.e., side holes or vents), have textures surfaces that induce turbulence (e.g., bumps, ribbing, etc.), have balloons, bellows, fins or turbines. A T-catheter configuration also finds use. The flow rate can also be increased in the distal portion of the outflow lumen, e.g., by high pressure injection or jetting.

The removal or withdrawing steps and the return steps can be performed concurrently, for parallel processing. This allows for a closed system and continuous processing or conditioning of the CSF, the advantages of which are described herein. Overall, the inflow and outflow rates can be equal or substantially equal. Active flow can be maintained using a pump, as discussed above for the systems. The active flow rate can be uniform or discontinuous, as needed. Also, the flow path direction of the CSF can be reversed, periodically, intermittently, or throughout the duration of a treatment, such that the inflow port becomes the outflow port and the outflow port becomes the inflow port.

In addition to removal of specific toxins from the CSF, the present methods contemplate the delivery of therapeutic agents on the return cycle. That is, after a given volume is passed through the specific purification schema of interest, a specific pharmacologic agent or drug can be administered directly to the CNS and bypass the blood brain barrier. This provides the opportunity for specific delivery of pharmaceuticals to the CNS without the often many systemic side effects associated with oral or intravenous delivery. One of the challenges of drug delivery via the CSF is designing the drug to penetrate the brain/spinal cord parenchyma. A variety of ways including adjusting the hydrophilicity or using liposome-based approaches in conjunction with the system described herein may be envisioned. Thus, for the first time, the system described herein allows for the combined removal of specific toxins as well as delivery of specific therapeutic agents to the CNS.

The present methods also contemplate the infusion of artificial CSF fluid into the system, if needed, at any time. The combined purification of CSF with return of artificial CSF with appropriate physical/chemical safeguards in addition to the purified CSF is but one possibility. The system may also be primed with such a physiologically compatible artificial CSF solution.

a. Methods of Ameliorating Disease Conditions i. Alzheimer's Disease (AD)

Alzheimer's disease (AD) is a progressive neurodegenerative disorder characterized by abnormal accumulations of amyloid plaques and neurofibrillary tangles. Amyloid plaque formation is thought to be partly due to failure of clearance of beta-amyloid protein (A). APP (amyloid precursor protein) generates various forms of amyloid A through enzymatic processing. See, Blennow, K., M. J. de Leon, et al. (2006). Lancet 368(9533): 387-403. Diffusible oligomers of A (from plaques) inhibit long term potentiation, cause membrane damage, alter membrane fluidity, and act as pore-forming toxins See, Caughey, B. and P. T. Lansbury (2003). Annu Rev Neurosci 26: 267-98; and Glabe, C. G. (2006). Neurobiol Aging 27(4): 570-5. In AD, tau proteins also aggregate, resulting in degeneration of neuronal axons and dendrites and producing neurofibrillary tangles. Tau protein accumulation leads to cellular oxidative stress, which may be a causal factor in tau-induced neurodegeneration. See, Dias-Santagata, D., T. A. Fulga, et al. (2007). J Clin Invest 117(1): 236-45. Specifically, highly reactive oxygen species oxidize lipids, proteins, and DNA, leading to tissue damage and cell death. These markers for oxidized lipids and proteins accumulate in regions that are particularly affected in neurodegenerative diseases. Markers of oxidative damage have been detected in brain tissue from patients with AD and other neurodegenerative disorders. See, Koo, E. H., P. T. Lansbury, Jr., et al. (1999). Proc Natl Acad Sci USA 96(18): 9989-90. Free radical injury also appears to be a fundamental pathophysiologic mediator of tissue injury in human disease, including acute ischemic stroke, amyotrophic lateral sclerosis, Parkinson's disease, and AD. See, Taylor, J. P., J. Hardy, et al. (2002). Science 296(5575): 1991-5. Current therapies for AD are only marginally effective, as they may not slow rate of neurodegeneration, and have significant side-effects and some (immunization strategies) are tentative at best.

In contrast, CSF processing of amyloid and tau proteins and neutralization of reactive oxidative species among others is both a symptomatic and disease-modifying treatment through its ability to reduce, limit, and prevent plaque and tangle formation as well as counteract neuroinflammation. It has the ability to address the disease process from multiple different perspectives based on our present day understanding of disease pathogenesis. It may also be safer due to lower risk of liver damage and brain inflammation compared to current pharmacologic and immunotherapeutic regimens, respectively.

Accordingly, the present methods provide for ameliorating or reducing the symptoms of Alzheimer's disease by reducing or eliminating the presence of beta-amyloid and/or tau proteins in the CSF using the systems described herein. The methods comprise removing CSF from a patient, as described herein; removing at least one of pathological proteins, including A and tau, and inflammatory mediators (e.g., cytokines, including TNF-a, IL-1, IL-2, IL-6, IL-12, interferon-y, etc.) from the CSF, and returning the endogenous CSF to the patient, wherein the removing and returning steps are performed concurrently during at least a portion of the treatment. In some embodiments, the A or tau proteins and/or inflammatory mediators are removed from the CSF using an immunoaffinity column or a size exclusion column, or both.

In another embodiment, the methods provide for ameliorating or reducing the symptoms of Alzheimer's disease by introducing a catheter apparatus through a spinal access site into a spinal CSF space of a patient; advancing the catheter apparatus through the spinal CSF space cranially toward the brain so that a distal port and a proximal port on the catheter apparatus are disposed within the CSF space and spaced-apart by a preselected distance or adjusted to an appropriate distance; withdrawing CSF through one of said ports; removing at least one of A or tau proteins or inflammatory mediators from the withdrawn CSF thereby conditioning the CSF; and returning the conditioned CSF through the other of said ports.

Further embodiments for treating Alzheimer's disease are as discussed above and herein.

i. Parkinson's Disease (PD)

Parkinson's disease (PD) is caused by a loss of dopamine-containing pigmented neurons in the substantia nigra. Free radical injury and formation of alpha-synuclein fibrils and oligomers (i.e., peptides) are involved in pathogenesis of PD. See, Steece-Collier, K., E. Manes, et al. (2002). Proc Natl Acad Sci USA 99(22): 13972-4. Current treatments (dopamine replacement therapy with L-dopa, Catechol-O-methyl transferase (COMT) inhibitors, amantadine and anti-cholinergic medications for symptomatic relief, surgery with deep brain stimulation) do not have a long-lasting effect, do not address the cause of disease and can have debilitation side-effects including dyskinesias. See, Dunnett, S. B. and A. Bjorklund (1999). Nature 399 (6738 Suppl): A32-9; Dawson, T. M. and V. L. Dawson (2003). Science 302 (5646): 819-22; and DeKosky, S. T. and K. Marek (2003). Science 302(5646): 830-4. There is a need for treatment that halts degeneration by removing free radicals and neurotoxic species. See, Shoulson, I. (1998). Science 282(5391): 1072-4. CSF filtration has fulfills that unmet medical need and can represent a disease-modifying mechanism for new PD treatments.

Accordingly, the present methods provide for ameliorating or reducing the symptoms of Parkinson's disease by reducing or eliminating the presence of alpha-synuclein fibrils and/or oligomers in the CSF using the systems described herein. The methods comprise removing CSF from a patient, as described herein; removing at least one of alpha-synuclein proteins and inflammatory mediators from the CSF, and returning the endogenous CSF to the patient, wherein the removing and returning steps are performed concurrently during at least a portion of the treatment. In some embodiments, the alpha-synuclein fibrils and oligomers are removed from the CSF using an immunoaffinity column or a size exclusion column, or both.

In another embodiment, the methods provide for ameliorating or reducing the symptoms of Parkinson's disease by introducing a catheter apparatus through a spinal access site into a spinal CSF space of a patient; advancing the catheter apparatus through the spinal CSF space cranially toward the brain such that a distal port and a proximal port on the catheter apparatus are disposed within the CSF space and spaced-apart by a preselected distance or adjusted to an appropriate distance; withdrawing CSF through one of said ports; removing at least one of alpha-synuclein proteins and inflammatory mediators from the withdrawn CSF thereby conditioning the CSF; and returning the conditioned CSF through the other of said ports.

Further embodiments for treating Parkinson's disease are as discussed above and herein.

i. Amyotrophic Lateral Sclerosis (ALS)

Amyotrophic lateral sclerosis (ALS)/Lou Gehrig's Disease is a rapidly progressive, invariably fatal motor neuron disease that attacks the nerve cells responsible for controlling voluntary muscles. See, Rowland, L. P. (1995). Proc Natl Acad Sci USA 92(5): 1251-3. Both the upper motor neurons and the lower motor neurons degenerate or die, ceasing to send messages to muscles. ALS patients had higher levels of glutamate in the serum and spinal fluid. Laboratory studies have demonstrated that neurons begin to die off when they are exposed over long periods to excessive amounts of glutamate. See, Rowland, L. P. (1995). Proc Natl Acad Sci USA 92(5): 1251-3. Increased levels of neurofilament protein were found in CSF of ALS patients as well as increased levels of antibodies against GM1-gangliosides, AGM1-gangliosides and sulfatides in 20%, 15%, 8% of CSF of ALS patients, respectively. See, Valentine, J. S. and P. J. Hart (2003). Proc Natl Acad Sci USA 100(7): 3617-22; and Banci, L., I. Bertini, et al. (2007). Proc Natl Acad Sci USA 104(27): 11263-7. Thus, antibodies may be implicated in ALS by impairing the function of motor neurons, interfering with the transmission of signals between the brain and muscle. Free radical injury is also likely to be involved in ALS. A marker of oxidative stress and lipid peroxidation, 4-hydroxynonenal (HNE), was elevated in the CSF of patients with sporadic ALS. Current clinical treatments for ALS (Riluzole) that reduce the amount of glutamate released do not reverse the damage already done to motor neurons and cause side-effects such as hepatotoxicity. In ALS, CSF purification would reduce excessively high glutamate levels in CSF and reduce oxidative species, thus prolonging the lifespan of motor neurons w/o serious side effects such as liver damage, and it would remove autoimmune antibodies and reactive oxidative species from CSF.

Accordingly, the present methods provide for ameliorating or reducing the symptoms of Amyotrophic lateral sclerosis (ALS) by reducing or eliminating the presence of one or more of insoluble superoxide dismutase-1 (SOD1), glutamate, neurofilament protein, and anti-GM1 ganglioside antibodies in the CSF using the systems described herein. The methods comprise removing CSF from a patient, as described herein; removing at least one of insoluble superoxide dismutase-1 (SOD1), glutamate, neurofiliment protein, and anti-GM1 ganglioside antibodies or other inflammatory mediators from the CSF, and returning the endogenous CSF to the patient, wherein the removing and returning steps are performed concurrently during at least a portion of the treatment. In some embodiments, the insoluble superoxide dismutase-1 (SOD1), glutamate, neurofilament protein, anti-GM1 ganglioside antibodies or other inflammatory mediators are removed from the CSF using one or more of an immunoaffinity column, a size exclusion column, an anionic exchange column, a cationic exchange column, and a Protein A or Protein G column.

In another embodiment, the methods provide for ameliorating or reducing the symptoms of Amyotrophic lateral sclerosis (ALS) by introducing a catheter apparatus through a spinal access site into a spinal CSF space of a patient; advancing the catheter apparatus through the spinal CSF space toward the brain so that a distal port and a proximal port on the catheter apparatus are disposed within the CSF space and spaced-apart by a preselected distance or adjusted to an appropriate distance; withdrawing CSF through one of said ports; removing at least one of insoluble superoxide dismutase-1 (SOD1), glutamate, neurofilament protein, anti-GM1 ganglioside antibodies or other inflammatory mediators from the withdrawn CSF thereby conditioning the CSF; and returning the conditioned CSF through the other of said ports.

Further embodiments for treating Amyotrophic lateral sclerosis (ALS) are as discussed above and herein.

a. Cerebral Vasospasm

Cerebral vasospasm is a time-dependent narrowing of cerebral vessel caliber, likely due to blood in the subarachnoid space (post cerebral aneurysm rupture, subarachnoid hemorrhage (SAH), craniocerebral trauma, bacterial meningitis, after surgery in the sellar/parasellar region, etc.). See, Macdonald, R. L., R. M. Pluta, et al. (2007). Nat Clin Pract Neurol 3(5): 256-63. Hemolysis is necessary for vasospasm to develop and oxyhemoglobin is believed to be one of the many vasoactive substance released. Elevated levels of oxyhemoglobin are maintained in the CSF over the duration of vasospasm. In contrast, most other vasoactive agents released after clot lysis are rapidly cleared from the CSF. See, Macdonald, R. L., R. M. Pluta, et al. (2007). Nat Clin Pract Neurol 3(5): 256-63. In subarachnoid patients with vasospasm, endothelin in the CSF remained at or increased above levels measured before surgery. The increase coincided with the appearance of vasospasm as documented by transcranial doppler and clinical symptoms. In SAH patients who did not develop vasospasm, the concentration of endothelin in the CSF decreased with time. See, Macdonald, R. L., R. M. Pluta, et al. (2007). Nat Clin Pract Neurol 3(5):

256-63. Current therapies (calcium channel blockers, hypervolemic, hypertensive therapy and hemodilution (HHH therapy)) are not effective in preventing vasospasm. CSF filtration is more likely to be therapeutic by early and direct removal of blood clot, red blood cells, platelets and the downstream cascades involving oxyhemoglobin and endothelin that lead to vasospasm.

Accordingly, the present methods provide for ameliorating or reducing the symptoms of cerebral vasospasm by reducing or eliminating the presence of one or more of blood cells (e.g., erythrocytes), hemoglobin, oxyhemoglobin, endothelin or other inflammatory mediators in the CSF using the systems described herein. The methods comprise removing CSF from a patient, as described herein; removing at least one of blood cells, hemoglobin, oxyhemoglobin, endothelin or inflammatory mediators from the CSF, and returning the endogenous CSF to the patient, wherein the removing and returning steps are performed concurrently during at least a portion of the treatment. In some embodiments, the oxyhemoglobin and endothelin are removed from the CSF using one or more of an immunoaffinity column, a size exclusion column, an anionic exchange column, and a cationic exchange column.

In another embodiment, the methods provide for ameliorating or reducing the symptoms of cerebral vasospasm by introducing a catheter apparatus through a spinal access site into a spinal CSF space of a patient; advancing the catheter apparatus through the spinal CSF space toward the brain so that a distal port and a proximal port on the catheter apparatus are disposed within the CSF space and spaced-apart by a preselected distance or adjusted to an appropriate distance; withdrawing CSF through one of said ports; removing at least one of blood cells, hemoglobin, oxyhemoglobin, endothelin or inflammatory mediators from the withdrawn CSF thereby conditioning the CSF; and returning the conditioned CSF through the other of said ports.

Further embodiments for treating cerebral vasospasm are as discussed above and herein.

i. Encephalitis

Encephalitis is inflammation of the brain due to multiple causes: HSV (herpes simplex virus), Lyme disease, syphilis, bacterial infection, etc. Infants younger than 1 year and adults older than 55 are at greatest risk of death from encephalitis. See, Vernino, S., M. Geschwind, et al. (2007). Neurologist 13(3): 140-7. Current therapies (corticosteroids to reduce brain swelling and NSAIDs to decrease fever) do not target the cause of encephalitis. Levels of sTNF-R (reflects biologic activity of TNF-alpha, a major inflammatory mediator) were significantly higher in the CSF and serum of children with acute encephalitis than in those of control subjects. See, Vernino, S., M. Geschwind, et al. (2007). Neurologist 13(3): 140-7. Levels of IgG were increased in herpes simplex encephalitis. See, Vernino, S., M. Geschwind, et al. (2007). Neurologist 13(3): 140-7. CSF processing could restore levels of TNF-alpha and IgG to physiologic levels, reduce inflammation and aid in removal of viruses, parasites, prions, fungi and bacteria. Further applications include treating victims of biologic warfare (anthrax, botulinum, ricin, saxitoxin, etc.) by directly removing the toxin of interest from attacking the CNS.

Accordingly, the present methods provide for ameliorating or reducing the symptoms of encephalitis by reducing or eliminating the presence of one or more of tumor necrosis factor-alpha (TNFa) and IgG in the CSF using the systems described herein. The methods comprise removing CSF from a patient, as described herein; removing at least one of TNFa and IgG or other inflammatory mediators from the CSF, and returning the endogenous CSF to the patient, wherein the removing and returning steps are performed concurrently during at least a portion of the treatment. In some embodiments, the TNFa and IgG are removed from the CSF using one or more of an immunoaffinity column, a size exclusion column, an anionic exchange column, a cationic exchange column and a Protein A or Protein G column.

In another embodiment, the methods provide for ameliorating or reducing the symptoms of encephalitis by introducing a catheter apparatus through a spinal access site into a spinal CSF space of a patient; advancing the catheter apparatus through the spinal CSF space toward the brain so that a distal port and a proximal port on the catheter apparatus are disposed within the CSF space and spaced-apart by a preselected distance or adjusted to an appropriate distance; withdrawing CSF through one of said ports; removing at least one of TNFa and IgG or other inflammatory mediators from the withdrawn CSF thereby conditioning the CSF; and returning the conditioned CSF through the other of said ports.

Further embodiments for treating encephalitis are as discussed above and herein.

a. Guillain Barre Syndrome (GB S)

Guillain Barre Syndrome (GBS) is divided into the two major subtypes: acute inflammatory demyelinating polyneuropathy (AIDP) and acute motor axonal neuropathy (AMAN). See, Parkhill, J., B. W. Wren, et al. (2000). Nature 403(6770): 665-8; and Yuki, N., K. Susuki, et al. (2004). Proc Natl Acad Sci USA 101(31): 11404-9. In Europe and North America, GBS is usually caused by AIDP with prominent lymphocytic infiltration of the peripheral nerves and macrophage invasion of myelin sheath and Schwann cells. Activated complement found in cerebrospinal fluid of Guillain-Barre and multiple sclerosis (MS) patients may contribute to demyelination. See, Parkhill, J., B. W. Wren, et al. (2000). Nature 403(6770): 665-8; and Yuki, N., K. Susuki, et al. (2004). Proc Natl Acad Sci USA 101(31): 11404-9. Treatment of GBS is subdivided into symptomatic management of severely paralyzed patients requiring intensive care and ventilatory support, and specific disease therapy to lessen the nerve damage. Immunomodulating treatments such as plasmapheresis and intravenous immunoglobulin are indicated for patients who are unable to walk independently. Results of international randomized trials have shown equivalent efficacy of both plasmapheresis and intravenous immunoglobulin, but corticosteroids are not effective. See, McKhann, G. M., J. W. Griffin, et al. (1988). Ann Neurol 23(4): 347-53; and Kuwabara, S., M. Mori, et al. (2001). Muscle Nerve 24(1): 54-8. Repeated filtration of CSF may remove pathogenetically relevant cells, immunoglobulins and polypeptides. Observations in 12 severe Guillain-Barre patients treated with CSF filtration indicate that it is a safe and effective procedure. CSF filtration and plasma exchange therapies were at least equally efficacious, and a patient with severe disease who did not respond to plasma exchange recovered completely with CSF filtration. See, Wollinsky, K. H., P. J. Hulser, et al. (2001). Neurology 57(5): 774-80. CSF filtration (in vitro testing) effectively removed cells and inflammatory mediators (e.g. C5a, TNF-α, IL-2, IL-6, interferon-y, IgG, endotoxins, and cells). See, Wollinsky, K. H., P. J. Hulser, et al. (2001). Neurology 57(5): 774-80. Thus, studies show that CSF filtration is at least as effective as plasmapheresis and it reduces, limits, and prevents nerve damage by removing lymphocytes, macrophages, complement proteins and other inflammatory agents.

Accordingly, the present methods provide for ameliorating or reducing the symptoms of Guillain Barre Syndrome (GB S) by reducing or eliminating the presence of one or more of cells and inflammatory mediators selected from the group consisting of C5a, TNF-a, IL-2, IL-6, interferon-y, IgG, and endotoxins in the CSF using the systems described herein. The methods comprise removing CSF from a patient, as described herein; removing at least one of cells and inflammatory mediators selected from the group consisting of C5a, TNF-a, IL-2, IL-6, interferon-y, IgG, and endotoxins from the CSF, and returning the endogenous CSF to the patient, wherein the removing and returning steps are performed concurrently during at least a portion of the treatment. In some embodiments, the cells and inflammatory mediators selected from the group consisting of C5a, TNF-a, IL-2, IL-6, interferon-y, IgG, and endotoxins are removed from the CSF using one or more of an immunoaffinity column, a size exclusion column, an anionic exchange column, a cationic exchange column and a Protein A or Protein G column.

In another embodiment, the methods provide for ameliorating or reducing the symptoms of Guillain Bane Syndrome (GBS) by introducing a catheter apparatus through a spinal access site into a spinal CSF space of a patient; advancing the catheter apparatus through the spinal CSF space toward the brain so that a distal port and a proximal port on the catheter apparatus are disposed within the CSF space and spaced-apart by a preselected distance or adjusted to an appropriate distance; withdrawing CSF through one of said ports; removing at least one of cells and inflammatory mediators selected from the group consisting of C5a, TNF-a, IL-2, IL-6, interferon-y, IgG, and endotoxins from the withdrawn CSF thereby conditioning the CSF; and returning the conditioned CSF through the other of said ports.

Further embodiments for treating Guillain Bane Syndrome are as discussed above and herein.

a. Multiple Sclerosis (MS)

Multiple sclerosis (MS) is the most common demyelinating disease in humans and has an unknown etiology. However, it is widely accepted to be an autoimmune disease mediated by autoreactive T lymphocytes with specificity for myelin antigens. See, Noseworthy, J. H. (1999). Nature 399 (6738 Suppl): A40-7. The pathologic hallmark of the disease is the MS plaque, an area of white matter demyelination usually accompanied by inflammatory infiltrate composed of T lymphocytes, some B cells and plasma cells, activated macrophages or microglial cells. IgG and complement are localized primarily at the periphery of plaques. B lymphocyte clones accumulate in the CSF of MS patients and patients with other neurological disorders. Anti-myelin-oligodendrocyte glycoprotein antibodies were detected in CSF from seven of the patients with MS, compared to two with other neurological diseases and one with tension headache. See, Hohlfeld, R. and H. Wekerle (2004). Proc Natl Acad Sci. USA 101 Suppl 2: 14599-606. Elevated numbers of CD4+ T helper cells can be found in the CSF during early exacerbations. Osteopontin is increased in patients' plasma before and during relapses and was found to induce worsening autoimmune relapses and severe progression of myelinating diseases. See, Hohlfeld, R. and H. Wekerle (2004). Proc Natl Acad Sci USA 101 Suppl 2: 14599-606. Current therapies are limited and often ineffective and include global immunosuppression mediated by steroids, interferon beta therapy, monoclonal antibody treatments and peptide fragments similar to myelin proteins. CSF purification would have the advantage of depletion cell populations and alleviated the effects of MS exacerbations by: 1) removal of autoreactive CD4+ and CD8+ T cells, 2) reduction in the levels of pro-inflammatory cytokines and 3) reduction in the production of autoreactive antibodies by B cells. Depletion of these autoreactive cell populations also can reduce the recurrence of MS exacerbations, limit permanent damage caused by the inflammation seen in an exacerbation, and prevent lesions that mark progression of the disease. By restricting this depletion to the CSF, the present systems and methods addresses these issues without many of the complications associated with steroid treatment or systemic immunosuppression.

Accordingly, the present methods provide for ameliorating or reducing the symptoms of multiple sclerosis (MS) by reducing or eliminating the presence of one or more of T cells, B cells, anti-myelin antibodies and inflammatory mediators selected from the group consisting of TNF-a, IL-2, IL-6, interferon-y in the CSF using the systems described herein. The methods comprise removing CSF from a patient, as described herein; removing at least one of T cells, B cells, anti-myelin antibodies and inflammatory mediators selected from the group consisting of TNF-a, IL-2, IL-6, interferon-y from the CSF, and returning the endogenous CSF to the patient, wherein the removing and returning steps are performed concurrently during at least a portion of the treatment. In some embodiments, the T cells, B cells, anti-myelin antibodies and inflammatory mediators selected from the group consisting of TNF-a, IL-2, IL-6, interferon-y are removed from the CSF using one or more of an immunoaffinity column, a size exclusion column, an anionic exchange column, a cationic exchange column and a Protein A or Protein G column.

In another embodiment, the methods provide for ameliorating or reducing the symptoms of multiple sclerosis (MS) by introducing a catheter apparatus through a spinal access site into a spinal CSF space of a patient; advancing the catheter apparatus through the spinal CSF space toward the brain so that a distal port and a proximal port on the catheter apparatus are disposed within the CSF space and spaced-apart by a preselected distance or adjusted to an appropriate distance; withdrawing CSF through one of said ports; removing at least one of T cells, B cells, anti-myelin antibodies and inflammatory mediators selected from the group consisting of TNF-a, IL-2, IL-6, interferon-y from the withdrawn CSF thereby conditioning the CSF; and returning the conditioned CSF through the other of said ports.

Further embodiments for treating multiple sclerosis (MS) are as discussed above and herein.

a. Stroke

Stroke occurs when a blood clot blocks an artery or a blood vessel breaks, interrupting blood flow to an area of the brain; brain cells then begin to die and brain damage occurs. Free radical injury is implicated in pathogenesis of stroke. CSF enolase was raised in patients with transient ischemic attacks and patients with complete strokes. See, McCulloch, J. and D. Dewar (2001). Proc Natl Acad Sci USA 98(20): 10989-91. A high cerebrospinal fluid enolase was always associated with a poor prognosis. Endothelin 1 (ET-1), a highly potent endogenous vasoactive peptide, exerts a sustained vasoconstrictive effect on cerebral vessels. See, Mascia, L., L. Fedorko, et al. (2001). Stroke 32(5): 1185-90; and Kessler, I. M., Y. G. Pacheco, et al. (2005). Surg Neurol 64 Suppl 1: S1:2-5; discussion S1:5. Elevation of ET-1 in plasma has been reported 1 to 3 days after ischemic stroke. Mean CSF concentration of ET-1 in the CSF of stroke patients was 16.06.+–0.4.9 pg/mL, compared with 5.51.+–0.1.47 pg/mL in the control group (P<0.001). See, Mascia, L., L. Fedorko, et al. (2001). Stroke 32(5): 1185 90; and Kessler, I. M., Y. G. Pacheco, et al. (2005). Surg Neurol 64 Suppl 1: S1:2-5, discussion S1:5. Current stroke management is ineffective and includes symptomatic treatment (surgery, hospital care, and rehabilitation) or canes a risk of brain hemorrhage (cerebral angioplasty and use of tissue plasminogen activator (tPA) to dissolve acute clot in vessel). Similarly, traumatic brain injury (TBI) or spinal cord injury (SCI) occurs when sudden trauma affects the brain or spinal cord following falls, motor vehicle accidents, assaults etc. Current treatment of TBI and SCI focuses on increasing independence in everyday life and rehabilitation (i.e. individual therapy). Moderate hypothermia is thought to limit deleterious metabolic processes that can exacerbate injury. CSF processing would allow for not only the removal of neuroinflammatory components such as enolase, ET-1 and free radicals but provide selective cooling to the CNS which is expected to be faster and more effective than systemic cooling, which is limited by shivering and the danger of severe cardiac arrhythmias.

Accordingly, the present methods provide for ameliorating or reducing the symptoms of stroke, traumatic brain injury (TBI), spinal cord injury (SCI) by reducing or eliminating the presence of one or more of endothelin and enolase or other inflammatory mediators in the CSF using the systems described herein. The methods comprise removing CSF from a patient, as described herein; removing at least one of endothelin and enolase from the CSF, and returning the endogenous CSF to the patient, wherein the removing and returning steps are performed concurrently during at least a portion of the treatment. In some embodiments, the endothelin and enolase or other inflammatory mediators are removed from the CSF using one or more of an immunoaffinity column, a size exclusion column, an anionic exchange column, a cationic exchange column and a Protein A or Protein G column. In some embodiments, the removed CSF is cooled to below physiological temperatures.

In another embodiment, the methods provide for ameliorating or reducing the symptoms of stroke, TBI, SCI by introducing a catheter apparatus through a spinal access site into a spinal CSF space of a patient; advancing the catheter apparatus through the spinal CSF space cranially toward the brain so that a distal port and a proximal port on the catheter apparatus are disposed within the CSF space and spaced-apart by a preselected distance or adjusted to an appropriate distance; withdrawing CSF through one of said ports; removing at least one of endothelin and enolase or other inflammatory mediators from the withdrawn CSF and/or cooling the CSF to varying degrees thereby conditioning the CSF; and returning the conditioned CSF through the other of said ports.

Further embodiments for treating stroke are as discussed above and herein.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A system for conditioning cerebrospinal fluid (CSF), said system comprising:

a catheter assembly including a first lumen with a plurality of inflow openings and a second lumen with a plurality of outflow openings, said catheter assembly being adapted to be introduced in a CSF space, each of the plurality of inflow openings being spaced an adjustable distance axially apart from each of the plurality of outflow openings;

a pump connectable between the first and second lumens to induce a flow of CSF therebetween; and a conditioning component connectable between the first and second lumens to condition the CSF flowing therebetween, and wherein the catheter assembly is configured as a closed loop system to withdraw CSF through the plurality of inflow openings and return CSF through the plurality of outflow openings at substantially the same rate without any artificial cerebrospinal fluid.

2. The system of claim 1, wherein the pump has a flow rate adjustable between 0.04 ml/min to 30 ml/min.

3. The system of claim 1, wherein the pump comprises a peristaltic pump which is isolated from the CSF flow.

4. The system of claim 1, wherein the condition component is selected from the group consisting of size exclusion, immunoaffinity, biospecific affinity, cationic exchange, anionic exchange and hydrophobicity.

5. The system of claim 1, wherein the system has a CSF retention volume below 40 ml.

6. The system of claim 1, wherein the conditioning component is configured to remove at least one of erythrocytes, hemoglobin, oxyhemoglobin and endothelin from the CSF.

7. The system of claim 1, wherein the conditioning component is configured to remove at least one of alpha-synuclein fibrils and oligomers from the CSF.

8. The system of claim 1, wherein the conditioning component is configured to remove at least one of insoluble superoxide dismutase-1 (SOD1), glutamate, neurofilament protein, and anti-GM1 ganglioside antibodies from the CSF.

9. The system of claim 1, wherein the conditioning component is configured to remove at least one of tumor necrosis factor-alpha (TNFa) and IgG from the CSF.

10. The system of claim 1, wherein the conditioning component is configured to remove at least one of cells and inflammatory mediators selected from the group consisting of C5a, TNF a, IL-2, IL-6, interferon-y, IgG, and endotoxins from the CSF.

11. The system of claim 1, wherein the conditioning component is configured to remove at least one of T cells, B cells, anti-myelin antibodies and inflammatory mediators selected from the group consisting of TNF-a, IL-2, IL-6, interferon-y from the CSF.

12. The system of claim 1, wherein the conditioning component is configured to remove at least one of endothelin and enolase from the CSF.

13. A system for conditioning cerebrospinal fluid (CSF), the system comprising:

a catheter having a first lumen with a plurality of aspiration openings and a second lumen having a plurality of infusion openings; and wherein each of the plurality of aspiration openings are spaced an adjustable distance axially apart from each of the plurality of infusion openings; wherein the first lumen is configured to remove a cerebrospinal fluid from a first cerebrospinal fluid space in a patient through the plurality of aspiration openings; a filter coupled to the catheter, the filter being designed to remove one or more materials from the cerebrospinal fluid and to form a conditioned cerebrospinal fluid; wherein the second lumen is configured to return the conditioned cerebrospinal fluid to a second cerebrospinal fluid space through the plurality of infusion openings; and wherein the system is configured as a closed loop system such that cerebrospinal fluid is removed from the patient at a first flow rate, wherein the conditioned cerebrospinal fluid is returned to the patient at a second flow rate that is substantially the same as the first flow rate without any artificial cerebrospinal fluid.

14. The system of claim 13, wherein the system is configured such that the flow directions of removing the cerebrospinal fluid and returning the conditioned cerebrospinal fluid are periodically reversed.

15. The system of claim 13, wherein the filter is designed to remove meningitis-related substances.

16. The system of claim 13, wherein the filter is designed to remove at least one of blood cells, hemoglobin, oxyhemoglobin, endothelin or inflammatory mediators from the CSF.

17. The system of claim 13, wherein the filter is designed to remove at least one of AO or tau proteins or inflammatory mediators from the CSF.

18. The system of claim 13, wherein the filter is designed to remove at least one of cells and inflammatory mediators selected from the group consisting of C5a, TNP-a, IL-2, IL-6, interferon-v, IgG, and endotoxins from the CSF.

19. The system of claim 13, further including one or more sensors for intermittent or continuous monitoring or sampling the cerebrospinal fluid for levels of one or more specific compounds or parameters of interest, wherein one or more sensors are utilized to serially sample and quantify levels of a specific compound or molecule in the CSF, and be used as an indication of how much the system has conditioned the CSF.

20. A method for conditioning cerebrospinal fluid (CSF), the method comprising:

removing cerebrospinal fluid from a first location in a cerebrospinal fluid space of the patient with a catheter assembly, the catheter assembly comprising:

a first lumen with a plurality of inflow openings and a second lumen with a plurality of outflow openings, said catheter assembly being adapted to be introduced in a CSF space, each of the plurality of inflow openings being spaced an adjustable distance axially apart from each of the plurality of outflow openings;

a pump connectable between the first and second lumens to induce a flow of CSF therebetween; and a conditioning component connectable between the first and second lumens to condition the CSF flowing therebetween;

conditioning the cerebrospinal fluid with the conditioning component; and returning the conditioned cerebrospinal fluid to the patient at a second location in the cerebrospinal fluid space of the patient, wherein the cerebrospinal fluid is returned to the patient at substantially the same flow rate at which it is removed;

wherein the conditioned cerebrospinal fluid is free of artificial cerebrospinal fluid.

* * * * *